United States Patent
Josse et al.

(10) Patent No.: US 10,537,437 B2
(45) Date of Patent: Jan. 21, 2020

(54) SPINAL CONSTRUCT AND METHOD

(71) Applicant: WARSAW ORTHOPEDIC, INC, Warsaw, IN (US)

(72) Inventors: Loic Josse, Yens Vaud (CH); Jorg Franke, Magdeburg (DE); Jean Charles Le Huec, Pessac (FR); Phillipe Lemaitre, Crozet (FR); Bertrand Peultier, Les Hopitaux Neufs (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 175 days.

(21) Appl. No.: 15/864,630

(22) Filed: Jan. 8, 2018

(65) Prior Publication Data

US 2019/0209335 A1 Jul. 11, 2019

Related U.S. Application Data

(63) Continuation of application No. 14/873,397, filed on Oct. 2, 2015, now Pat. No. 9,883,952.

(51) Int. Cl.
*A61F 2/44* (2006.01)
*A61F 2/30* (2006.01)
*A61F 2/46* (2006.01)
*A61B 17/70* (2006.01)

(52) U.S. Cl.
CPC ........ *A61F 2/4425* (2013.01); *A61F 2/30771* (2013.01); *A61F 2/4611* (2013.01); *A61B 17/7002* (2013.01); *A61F 2002/30092* (2013.01); *A61F 2002/30125* (2013.01); *A61F 2002/30131* (2013.01); *A61F 2002/30133* (2013.01); *A61F 2002/30156* (2013.01); *A61F 2002/30242* (2013.01); *A61F 2002/30405* (2013.01); *A61F 2002/30507* (2013.01); *A61F 2002/30528* (2013.01); *A61F 2002/30579* (2013.01); *A61F 2002/30607* (2013.01); *A61F 2002/30616* (2013.01); *A61F 2002/30617* (2013.01); *A61F 2002/30665* (2013.01); *A61F 2002/30774* (2013.01); *A61F 2002/30777* (2013.01); *A61F 2002/443* (2013.01); *A61F 2002/4623* (2013.01); *A61F 2002/4627* (2013.01); *A61F 2310/00017* (2013.01); *A61F 2310/00023* (2013.01); *A61F 2310/00029* (2013.01); *A61F 2310/00293* (2013.01); *A61F 2310/00359* (2013.01)

(58) Field of Classification Search
CPC .......................... A61F 2/4425; A61F 2/30771
See application file for complete search history.

(56) References Cited

U.S. PATENT DOCUMENTS

| | | | |
|---|---|---|---|
| 4,554,914 A * | 11/1985 | Kapp | ................. A61B 17/7068 606/247 |
| 6,106,557 A | 8/2000 | Robioneck et al. | |
| 7,744,650 B2 | 6/2010 | Lindner et al. | |

(Continued)

*Primary Examiner* — Christian A Sevilla

(57) ABSTRACT

A spinal construct includes a first endplate that is configured to engage a first vertebral surface. An expandable member is connected with the first endplate and includes a mating element. A second endplate is configured to engage a second vertebral surface and includes an in-situ guide surface engageable with the mating element to connect the member with the second endplate. Systems and methods are disclosed.

20 Claims, 24 Drawing Sheets

(56) References Cited

U.S. PATENT DOCUMENTS

| | | |
|---|---|---|
| 8,377,140 B2 * | 2/2013 | DeFalco .................. A61F 2/44 |
| | | 254/100 |
| 8,668,740 B2 | 3/2014 | Rhoda et al. |
| 8,690,886 B2 | 4/2014 | Fedorov et al. |
| 8,870,880 B2 | 10/2014 | Himmelberger et al. |
| 9,211,197 B2 | 12/2015 | Baynham |
| 2006/0041313 A1 * | 2/2006 | Allard ................ A61B 17/1757 |
| | | 623/17.15 |
| 2009/0043391 A1 * | 2/2009 | de Villiers ............ A61F 2/4425 |
| | | 623/17.16 |
| 2015/0025636 A1 | 1/2015 | Lim et al. |
| 2016/0095716 A1 | 4/2016 | Baynham |

* cited by examiner

SPINAL CONSTRUCT AND METHOD

CROSS-REFERENCE TO RELATED APPLICATIONS

This application is a continuation of application U.S. patent application Ser. No. 14/873,397, filed on Oct. 2, 2015, which is hereby incorporated by reference herein, in its entirety.

TECHNICAL FIELD

The present disclosure generally relates to medical devices for the treatment of musculoskeletal disorders, and more particularly to a spinal construct configured for disposal with spaced vertebrae and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior technologies.

SUMMARY

In one embodiment, a spinal construct is provided. The spinal construct includes a first endplate that is configured to engage a first vertebral surface. An expandable member is connected with the first endplate and includes a mating element. A second endplate is configured to engage a second vertebral surface and includes an in-situ guide surface engageable with the mating element to connect the member with the second endplate. In some embodiments, systems and implants are disclosed.

In one embodiment, a method for treating a spine disorder is provided. The method comprises the steps of: delivering a first endplate with a first holder extending laterally therefrom about vertebral tissue along a substantially posterior approach and adjacent a first vertebral surface; connecting a first stabilizer with the first holder and the first vertebral surface; delivering a second endplate with a second holder extending laterally therefrom about vertebral tissue along a substantially posterior approach and adjacent a second vertebral surface; connecting a second stabilizer with the second holder and the second vertebral surface; delivering a member along a substantially posterior approach for disposal between the endplates; and removing the holders and the stabilizers from adjacent the vertebral surfaces.

BRIEF DESCRIPTION OF THE DRAWINGS

The present disclosure will become more readily apparent from the specific description accompanied by the following drawings, in which.

DETAILED DESCRIPTION

Figure 1:
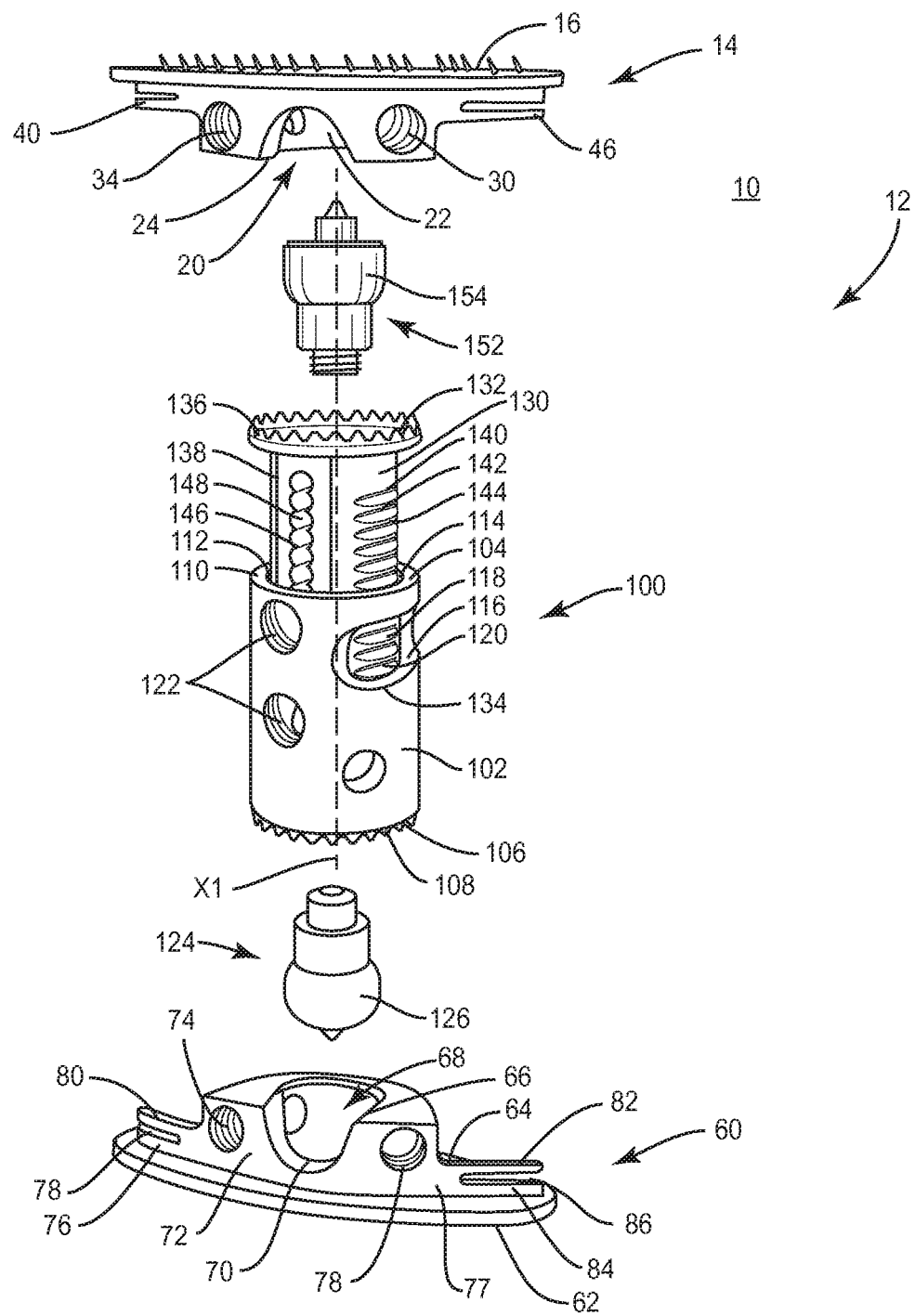
FIG. 1 is a perspective view of components of one embodiment of a spinal implant system in accordance with the principles of the present disclosure with parts separated.

The exemplary embodiments of a surgical system and related methods of use disclosed are discussed in terms of medical devices for the treatment of musculoskeletal disorders and more particularly, in terms of a spinal implant system that includes a spinal construct configured for disposal with spaced vertebrae and a method for treating a spine.

In some embodiments, the spinal implant system is employed with a method for a vertebral body replacement (VBR) and supplemental posterior spinal fixation in only one posterior approach. In some embodiments the spinal implant system includes specialized VBR endplates. In some embodiments, the endplates are pre-placed and/or fixed in position by connection to posterior screws and then combined in-situ with an expansion portion of a VBR device to create an assembled expandable VBR construct from a posterior approach.

In some embodiments, the spinal implant system includes an open endplate including channels for receiving ball connectors on ends of the expandable VBR construct. In some embodiments, the spinal implant system includes connections for pre-placement and endplate stabilization. In some embodiments, the spinal implant system includes a posterior fixator connector. In some embodiments, the posterior fixator connector is added to an existing/pre-placed VBR construct after expansion by virtue of a clamp attachment.

In some embodiments, the spinal implant system is employed with a method for vertebral body replacement (VBR) via a posterior approach. In some embodiments, the method is employed with a single posterior approach. In some embodiments, the method includes a step of posterior decompression and an anterior reconstruction along the same surgical posterior approach. In some embodiments, the spinal implant system and method provide a decrease in surgery time, a decrease in morbidity for the patient, and a surgical technique where endplates are inserted initially to provide a larger vertebral endplate coverage.

In some embodiments, the spinal implant system includes a posterior endplate. In some embodiments, the endplate includes a gripping zone. In some embodiments, the endplate includes a footprint. In some embodiments, the surgical system includes a ramp to guide VBR device insertion. In some embodiments, the spinal implant system includes an implant holder. In some embodiments, the implant holder is moved in a lateral direction+/− in alignment with a pedicle. In some embodiments, the spinal implant system includes an endplate holder. In some embodiments, the endplate holder is configured to grab the endplate above a superior nerve root.

In some embodiments, the spinal implant system is employed with a method for segment stabilization and bone resection. In some embodiments, the method provides segment stabilization with a rod. In some embodiments, the rod is one size. In some embodiments, the method facilitates resection of a vertebra.

In some embodiments, the spinal implant system is employed with a method for endplate placement. In some embodiments, the method includes the step of introducing a first endplate and inserting the first endplate with an endplate holder. In some embodiments, the first endplate is inserted laterally through the dural sac. In some embodiments, the first endplate is then rotated in between a first vertebra and a second vertebra. In some embodiments, the endplates are narrow in depth and large in width and are configured to facilitate insertion while keeping contact with a large surface area of bone.

In some embodiments, the spinal implant system includes an endplate stabilizer. In some embodiments, the method includes locking the first endplate into a position with the endplate stabilizer. In some embodiments, the method includes inserting a superior endplate with a Kerrison endplate holder below the superior nerve root. In some embodiments, a standard endplate holder is then screwed to the endplate, passing above the superior nerve root. In some embodiments, a second endplate is then placed in the same manner as the first endplate. In some embodiments, both endplates are locked in place. In some embodiments, endplate placement is checked by fluoroscopic control.

In some embodiments, the spinal implant system includes an expandable VBR device. In some embodiments, the spinal implant system is employed with a method that includes aligning the expandable VBR device with endplate ramps. In some embodiments, the expandable VBR device is then inserted in between the endplates and expanded. In some embodiments, the spinal implant system includes a VBR break off locking screw. In some embodiments, the method includes locking the expandable VBR device with the break off locking screw. In some embodiments, the method includes tightening the break off locking screw and when tightening is finalized and proper torque is achieved, breaking the locking screw.

In some embodiments, the spinal implant system includes an endplate break off locking screw and spacers. In some embodiments, the spacers are disposable. In some embodiments, the spacers are blue. In some embodiments, the method includes removing the spacers. In some embodiments, the method includes locking the endplates via tightening the endplate break off locking screw until it breaks at the proper torque. In some embodiments, the method provides secured placement of the endplates. In some embodiments, the method includes removing and disposing of the broken parts of the endplate locking screws. In some embodiments, the method includes removing endplate stabilizers and endplate holders. In some embodiments, the method provides posterior support. In some embodiments, a second rod is inserted into the pedicle screws and final tightening of the break off nut is performed after appropriate posterior compression. In some embodiments, the spinal implant system includes a VBR posterior fixator. In some embodiments, the VBR posterior fixator aids in stabilizing the spinal implant system. In some embodiments, the method includes attaching a VBR posterior fixator, which includes a rod via clipping onto the expandable VBR device and linking to a posterior construct. In some embodiments, the method includes tightening the VBR fixator rod such that the connection with the expandable VBR device is locked. In some embodiments, the method includes locking the rod via a TSRH-3D small connector.

In some embodiments, the spinal implant system includes a VBR posterior link. In some embodiments, the spinal implant system includes a first and a second endplate break off setscrew. In some embodiments, the surgical system includes a first posterior endplate. In some embodiments, the surgical system includes a first endplate ball joint. In some embodiments, the surgical system includes an expandable centerpiece. In some embodiments, the surgical system includes a second endplate ball joint. In some embodiments, the surgical system includes a second posterior endplate.

In some embodiments, the spinal implant system includes an endplate inserter. In some embodiments, the spinal implant system includes a spacer. In some embodiments, the spinal implant system includes a short screwdriver. In some embodiments, the spinal implant system includes a spur gear key. In some embodiments, the spinal implant system includes a VBR expander. In some embodiments, the spinal implant system includes a long screwdriver. In some embodiments, the spinal implant system includes an implant holder.

In some embodiments, the spinal implant system includes compact VBR implants and instruments. In some embodiments, the spinal implant system includes lengthened endcap holders. In some embodiments, the spinal implant system includes a perpendicular extension with a push button for release. In some embodiments, an endcap setscrew is disposed at an end of the perpendicular extension. In some embodiments, the spinal implant system includes ball joints that are configured for disposal at opposing ends of an expandable centerpiece. In some embodiments, three lengths of the centerpiece are available. In some embodiments, endcap height and a bottom portion of the ramp are lowered. In some embodiments, the spinal implant system includes a slide in and a fall in design. In some embodiments, the spinal implant system includes a VBR expander that includes a spur gear. In some embodiments, the spur gear is directly driven with a handle. In some embodiments, the spinal implant system includes a locking screw. In some embodiments, the locking screw includes a thread that is preceded by a taper. In some embodiments, the taper is configured to prevent any abutment with the expandable centerpiece.

In some embodiments, the spinal implant system includes compact VBR implants and instruments that are configured for vertebral body replacement by a posterior surgical approach. In some embodiments, the spinal implant system includes a calibrator. In some embodiments, the calibrator includes a mechanical function configured to lock a position during distraction. In some embodiments, the spinal implant system includes an endcap holder. In some embodiments, endcap gripping and setscrew tightening are separate functions. In some embodiments, the locking screw is configured to be inserted, tightened and sheared.

In some embodiments, the spinal implant system includes a centerpiece. In some embodiments, the spinal implant system includes a plurality of centerpieces. In some embodiments, the centerpieces are configured for engagement at opposing ends with a first ball joint and a second ball joint, and are specific for a TLIF approach. In some embodiments, the centerpiece includes two designs and is available in three sizes. In some embodiments, the centerpieces are configured in various sizes and dimensions. In some embodiments, a slide in centerpiece having a collapsed height with two endcaps is 29 mm, 33 mm or 39 mm. In some embodiments, a slide in centerpiece having an expanded height with two endcaps is 34 mm, 42 mm or 54 mm. In some embodiments, a slide in centerpiece having a minimal height between endcaps allowing centerpiece insertion is 29 mm, 33 mm or 39 mm. In some embodiments, a fall in centerpiece having a collapsed height with two endcaps is 29 mm, 33 mm or 39 mm. In some embodiments, a fall in centerpiece having an expanded height with two endcaps is 34 mm, 42 mm or 54 mm. In some embodiments, a fall in centerpiece having a minimal height between endcaps allowing centerpiece insertion is 32 mm, 36 mm or 42 mm.

In some embodiments, the endcaps include footprints that are decreased. In some embodiments, the endcap holder includes a perpendicular extension with a release button disposed on a shaft. In some embodiments, the spinal implant system includes stabilizing clamps. In some embodiments, the stabilizing clamps are configured for an open clamping design for endcap holder connection to the pedicle screw. In some embodiments, the calibrator includes ball ends configured similar and/or identical to a portion of the centerpiece for engagement. In some embodiments, the ball ends engage into an endcap socket joint. In some embodiments, the calibrator includes visual indicia. In some embodiments, the visual indicia includes a laser marked ruler that indicates an appropriate centerpiece size to select.

In some embodiments, the calibrator is configured to facilitate assembling of endcaps with an expandable centerpiece at a selected lordosis/kyphosis angle prior to implantation, for anterior, antero-lateral and lateral surgical approaches. In some embodiments, a method of employing the spinal implant system includes setting a lordosis/kyphosis angle(s) by selecting an endcap socket(s); inserting selected endcaps into an appropriate socket housing; assembling two sockets onto a frame and placing a centerpiece between a provisional shaft; aligning the provisional shaft with the angle corresponding to the surgical approach; and tightening each endcap screw with a screw driver.

In some embodiments, a method of employing the spinal implant system includes setting a lordosis/kyphosis angle(s) by selecting an endcap socket at 0, 5, 10, 15 or 20 angular degrees; inserting a selected first endcap into a socket slot; placing a centerpiece on the socket with a provisional shaft; positioning the provisional shaft to the angle corresponding to the surgical approach; tightening an endcap screw with a screw driver; returning the construct up-side-down; and repeating previous operations for a second endcap. In some embodiments, the method facilitates visualization of the lordosis/kyphosis angles with regard to the orientation given to the VBR inserter and the surgical approach.

In some embodiments, the method provides for a VBR via a posterior lumbar approach. In some embodiments, the method provides access to posterior structures. In some embodiments, pedicle screws are placed on one side of a surgical site. In some embodiments, a first endcap is inserted between two nerve roots using a Kerrison type implant holder. In some embodiments, the implant holder is reconnected to an endcap holder below the inferior root. In some embodiments, a second endcap is directly inserted with the endcap holder. In some embodiments, a calibrator is inserted into the resection of a vertebral body along with ball ends of an instrument into the endcap socket joint. In some embodiments, after the end cap position is adjusted with the calibrator, distraction is then applied to the endcaps so that teeth disposed on the endcaps impact into the vertebral endplates. In some embodiments, distraction is applied to determine the size of the centerpiece to implant. In some embodiments, an x-ray is used to determine the distance between the endcaps and the vertebral endplates. In some embodiments, stable positioning of the endcaps is ensured via connection to the pedicle screws via the stabilizing clamps.

In some embodiments, the calibrator maintains constant pressure on the endcaps during the connection of the stabilizing clamps to the pedicle screws. In some embodiments, the calibrator includes a locking feature configured to prevent distraction force during connection. In some embodiments, the calibrator includes arms. In some embodiments, the calibrator arms are stiff and/or non-flexible.

In some embodiments, the method includes the step of connecting the expandable centerpiece to the VBR expander, and then inserting the VBR expander into a vertebral defect. In some embodiments, the VBR expander is then disposed in between endcaps. In some embodiments, the spinal implant system includes ball and socket joints that are assembled together. In some embodiments the centerpiece is expanded. In some embodiments, a locking screw is inserted. In some embodiments the method includes x-ray control to verify proper tightening of the locking screw. In some embodiments, the locking screw includes a rounded tip. In some embodiments, the rounded tip translates beyond a posterior wall of the centerpiece. In some embodiments, endcap holders are released by pressing a push button to tighten the endcap setscrews. In some embodiments, pressure is added to the endcap holders to maintain contact with the endcaps while the setscrews are tightened. In some embodiments, the endcap holder includes a handle. In some embodiments, the handle is removable. In some embodiments, the functions of the endcap holder and setscrew holder are separated. In some embodiments, a posterior link is damped to the centerpiece and is fixed to a posterior rod. In some embodiments, the posterior link is configured to provide an efficient supplemental fixation to ensure good stability of the final construct through the same surgical approach. In some embodiments, the spinal implant system provides ease and speed for connecting the posterior link to the posterior rod.

In some embodiments, the spinal implant system includes a 29-34 mm expandable centerpiece combined with endcaps. In some embodiments, the spinal implant system includes a 33-42 mm expandable centerpiece combined with endcaps. In some embodiments, the spinal implant system includes a 39-54 mm expandable centerpiece combined with endcaps. In some embodiments, the spinal implant system includes a locking screw, a first endplate inserter, a second endplate inserter, a small connector and/or a posterior link.

In some embodiments, the spinal implant system includes a plurality of instruments. In some embodiments, the spinal implant system includes a first endplate inserter, a second endplate inserter, a modified Kerrison surgical instrument, a stabilizing clamp, a handle, a nut driver, a calibrator, VBR inserter, a spur gear key and/or a long nut driver.

In one embodiment, one or all of the components of the spinal implant system are disposable, peel-pack, pre-packed sterile devices used with an implant. One or all of the components of the spinal implant system may be reusable. The spinal implant system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, infection, such as, for example, tuberculosis, and fractures. In some embodiments, the present disclosure may be employed with other osteal and bone related applications, including those associated with diagnostics and therapeutics. In some embodiments, the disclosed spinal implant system and methods may be alternatively employed in a surgical treatment with a patient in a prone or supine position, and/or employ various surgical approaches to the spine, including anterior, posterior, posterior mid-line, direct lateral, postero-lateral, and/or anterolateral approaches, and in other body regions. The present disclosure may also be alternatively employed with procedures for treating the lumbar, cervical, thoracic, sacral and pelvic regions of a spinal column. The spinal implant system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
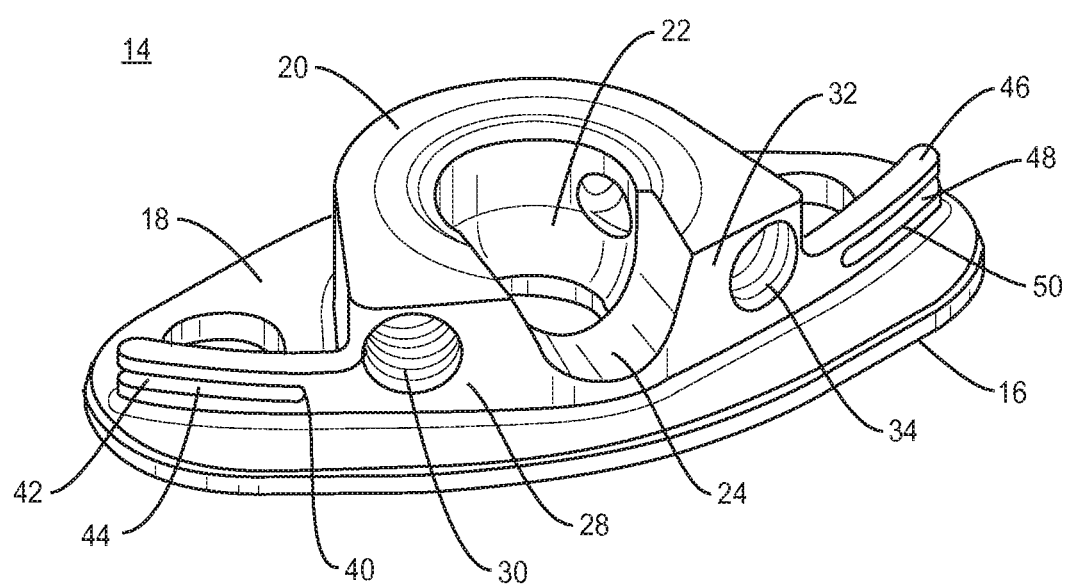
FIG. 2 is a perspective view of components of the system shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-2, there is illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 10 may be employed with surgical procedures, such as, for example, corpectomy and discectomy, which include fusion and/or fixation treatments that employ implants, to restore the mechanical support function of vertebrae.

Spinal implant system 10 includes a spinal construct 12. In some embodiments, spinal construct 12 comprises a VBR device. In some embodiments, spinal construct 12 comprises a plurality of members assembled for implantation with a body of a patient during a surgical procedure, as described herein. In some embodiments, spinal construct 12 comprises endplates that are pre-positioned and fixed with vertebral tissue via posterior screws. In some embodiments, the endplates of spinal construct 12 are assembled in-situ, as described herein, with an expansion portion and/or centerpiece, such as, for example, a spinal implant 100 described herein, which comprises an assembled expandable spinal construct 12.

Spinal construct 12 includes a member, such as, for example, an endplate 14. Endplate 14 includes a surface 16 configured to engage vertebrae, as described herein. Surface 16 is substantially planar. In some embodiments, all or only a portion of surface 16 may be arcuate, concave, convex, undulating and/or angled. In some embodiments, surface 16 can have cross-hatch texturing, spikes, barbs, raised elements, a porous titanium coating, and/or be rough, textured, porous, semi-porous, dimpled and/or polished such that it facilitates engagement with tissue. In some embodiments, the vertebral tissue may include intervertebral tissue, endplate surfaces and/or cortical bone.

Endplate 14 includes a surface 18. Surface 18 includes a wall 20 that defines a cavity 22. Cavity 22 is configured for engagement with a mating element of a member, such as, for example, an expandable spinal implant 100, as described herein. In some embodiments, cavity 22 may have various cross section configurations, such as, for example, circular, oval, oblong, triangular, rectangular, square, polygonal, irregular, uniform, non-uniform, variable and/or tapered.

Wall 20 defines an in-situ guide surface, such as, for example, a ramp 24. Ramp 24 includes a tapered configuration including surfaces of wall 20 that taper outwardly from surface 16. In some embodiments, ramp 24 has a U-shaped configuration. In some embodiments, all or only a portion of ramp 24 may be arcuate, concave, convex, undulating, funnel shaped and/or angled.

Ramp 24 is configured to facilitate alignment and translation of implant 100 into cavity 22 by guiding implant 100 along the surfaces of ramp 24 into cavity 22, as described herein. In some embodiments, in-situ guidance of one or more of the components of spinal construct 12 includes assembly of the components of spinal construct 12 in place, in position, within, on or about the body of a patient and/or at a surgical site, and/or adjacent to selected tissue for implantation of spinal construct 12 with the selected tissue. In some embodiments, in-situ guidance of one or more of the components of spinal construct 12 includes assembly of the components of spinal construct 12 in-vivo with a body of a patient. In some embodiments, endplate 14 is configured for engagement with vertebrae and is fixed in position and then assembled in-vivo with implant 100 during a surgical procedure, as described herein.

Wall 20 includes a surface 28 that defines an opening 30 disposed adjacent ramp 24. Opening 30 is configured for engagement with a surgical instrument, such as, for example, an inserter support 162, as shown in FIGS. 3-6, that comprises a portion of a provisional frame 160 to stabilize components of spinal implant system 10 during implantation of spinal construct 12 with the selected tissue, as described herein. In some embodiments, opening 30 is threaded for a threaded engagement with inserter support 162, as described herein.

Wall 20 includes a surface 32 that defines an opening 34 disposed adjacent ramp 24. Opening 34 is configured for engagement with an inserter support 162, as described herein. In some embodiments, opening 34 is threaded for a threaded engagement with inserter support 162, as described herein. Opening 34 is disposed on an opposite side of ramp 24 from opening 30, as shown in FIG. 2. Openings 30, 34 can be disposed in various and/or relative positions with endplate 14 to facilitate manipulation, introduction, delivery and/or implantation during a surgical procedure, and/or along surgical pathways, such as, for example, posterior, oblique, lateral and/or anterior. In some embodiments, opening 34 may be disposed at alternate orientations, relative to opening 30, such as, for example, parallel, transverse, perpendicular and/or other angular orientations such as acute or obtuse, co-axial and/or may be offset or staggered.

Surface 18 includes a wall 40. Wall 40 includes a surface 42 that defines a groove 44. Groove 44 is configured for engagement with a surgical instrument, such as, for example, an inserter 190 (FIGS. 7 and 8), as described herein. Surface 18 includes a wall 46. Wall 46 includes a surface 48 that defines a groove 50. Groove 50 is configured for engagement with inserter 190. Wall 46 is disposed on an opposite side of ramp 24 from wall 40, as shown in FIG. 2.

Spinal construct 12 includes a member, such as, for example, an endplate 60. Endplate 60 includes a surface 62 configured to engage vertebrae, as described herein. Surface 62 is substantially planar. In some embodiments, all or only a portion of surface 62 may be arcuate, concave, convex, undulating and/or angled. In some embodiments, surface 62 can have cross-hatch texturing, spikes, barbs, raised elements, a porous titanium coating, and/or be rough, textured, porous, semi-porous, dimpled and/or polished such that it facilitates engagement with tissue. In some embodiments, endplate 60 may be similarly or alternately configured relative to endplate 14.

Endplate 60 includes a surface 64. Surface 64 includes a wall 66 that defines a cavity 68. Cavity 68 is configured for engagement with a mating element of implant 100, as described herein. In some embodiments, cavity 68 may have various cross section configurations, such as, for example, circular, oval, oblong, triangular, rectangular, square, polygonal, irregular, uniform, non-uniform, variable and/or tapered.

Wall 66 defines an in-situ guide surface, such as, for example, a ramp 70. Ramp 70 includes a tapered configuration including surfaces of wall 66 that taper outwardly from surface 62. In some embodiments, ramp 70 has a U-shaped configuration. In some embodiments, all or only a portion of ramp 70 may be arcuate, concave, convex, undulating, funnel shaped and/or angled.

Ramp 70 is configured to facilitate alignment and translation of implant 100 into cavity 68 by guiding implant 100 along the surfaces of ramp 70 into cavity 68, as described herein. In some embodiments, endplate 60 is configured for engagement with vertebrae and is fixed in position and then assembled in-vivo with implant 100 during a surgical procedure, as described herein.

Wall 66 includes a surface 72 that defines an opening 74 disposed adjacent ramp 70. Opening 74 is configured for engagement with an inserter support 162, as described herein. In some embodiments, opening 74 is threaded for a threaded engagement with an inserter support 162, as described herein.

Wall 66 includes a surface 76 that defines an opening 78 disposed adjacent ramp 70. Opening 78 is configured for engagement with an inserter support 162, as described herein. In some embodiments, opening 78 is threaded for a threaded engagement with inserter support 162, as described herein. Opening 78 is disposed on an opposite side of ramp 70 from opening 74. Openings 74, 78 can be disposed in various and/or relative positions with endplate 60 to facilitate manipulation, introduction, delivery and/or implantation during a surgical procedure, and/or along surgical pathways, such as, for example, posterior, oblique, lateral and/or anterior. In some embodiments, opening 78 may be disposed at alternate orientations, relative to opening 74, such as, for example, parallel, transverse, perpendicular and/or other angular orientations such as acute or obtuse, co-axial and/or may be offset or staggered.

Surface 64 includes a wall 77. Wall 77 includes a surface 79 that defines a groove 80. Groove 80 is configured for engagement with an inserter 190 (FIGS. 7 and 8), as described herein. Surface 62 includes a wall 82. Wall 82 includes a surface 84 that defines a groove 86. Groove 86 is configured for engagement with an inserter 190. Wall 82 is disposed on an opposite side of ramp 70 from wall 77.

Implant 100 includes an outer body 102 having a tubular configuration. Body 102 extends in a linear configuration and defines a longitudinal axis X1. In some embodiments, body 102 may extend in alternate configurations, such as, for example, arcuate, offset, staggered and/or angled portions, which may include acute, perpendicular and obtuse.

Body 102 extends between an end 104 and an end 106. End 106 defines an end face 108 that is configured to engage endplate 60, as described herein. In some embodiments, end face 108 can include a surface that may be rough, textured, porous, semi-porous, dimpled and/or polished.

Body 102 includes a wall, such as, for example, a tubular wall 110. Wall 110 includes an inner surface 112 that defines an axial cavity 114 extending between ends 104, 106. In some embodiments, wall 110 includes a cylindrical cross-section. In some embodiments, the cross-section geometry of wall 110 may have various configurations, such as, for example, round, oval, oblong, triangular, polygonal having planar or arcuate side portions, irregular, uniform, non-uniform, consistent, variable, horseshoe shape, U-shape or kidney bean shape.

Wall 110 includes an inwardly oriented surface 116 that defines a lateral cavity, such as, for example, a side window 118. Window 118 includes an aperture, such as, for example, an opening 120. Opening 120 is configured for disposal of an instrument utilized to facilitate expansion of body 102 and a member, such as, for example, an inner body 130 of implant 100, as described herein. Opening 120 is oriented for disposal of a surgical instrument, such as, for example, an inserter (not shown) configured for engagement with gear teeth of body 130. Opening 120 is oriented substantially transverse, such as, for example, perpendicular to axis X1. In some embodiments, opening 120 may be variously oriented relative to axis X1, such as, for example, parallel or angled, which may include acute and obtuse orientations. In some embodiments, wall 120 may include one or a plurality of openings. In some embodiments, opening 120 may be variously configured, such as, for example, circular, oval, oblong, triangular, polygonal having planar or arcuate side portions, irregular, uniform, non-uniform, consistent, variable, horseshoe shape, U-shape or kidney bean shape.

In some embodiments, wall 110 defines openings 122 configured to receive an agent, which may include bone graft (not shown) and/or other materials, as described herein, for employment in a fixation or fusion treatment used for example, in connection with a corpectomy.

Figure 15:
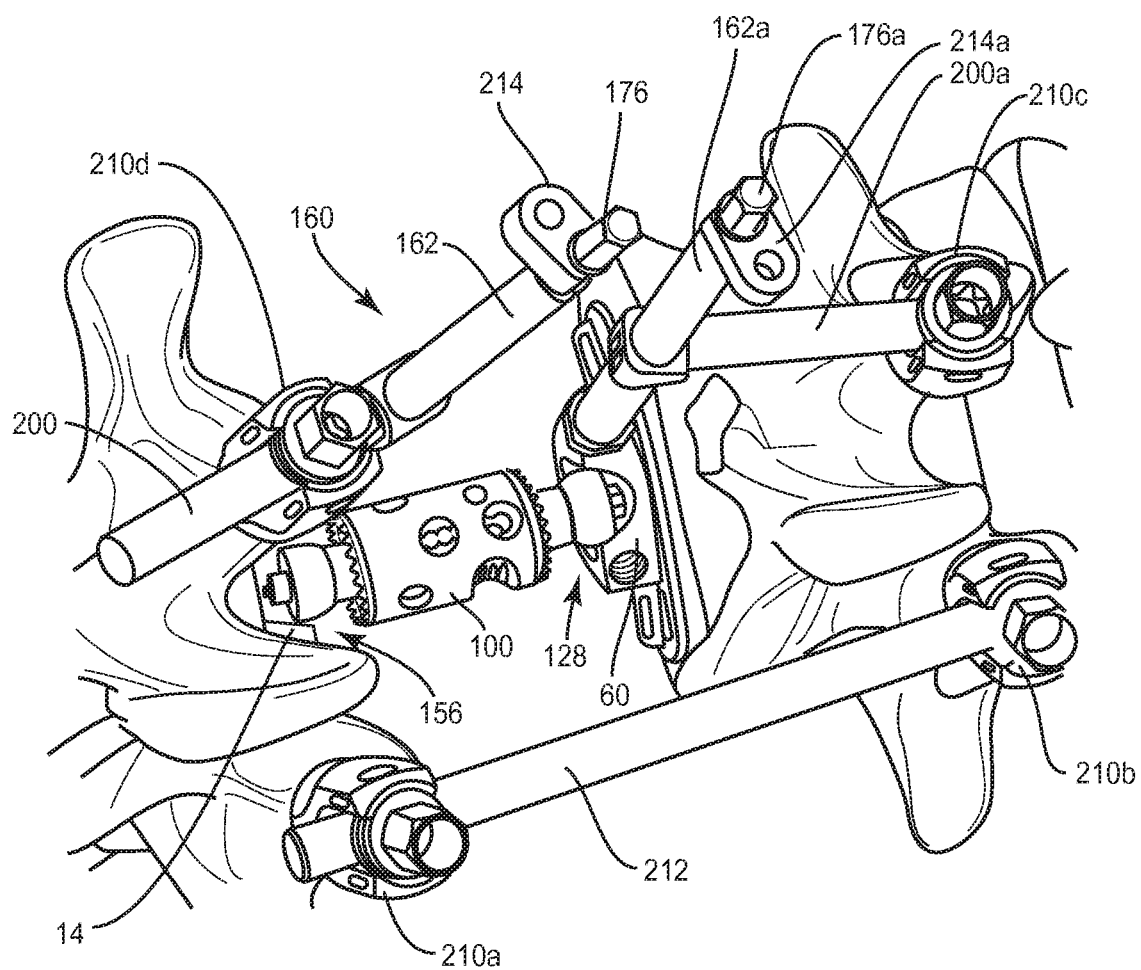
FIG. 15 is a perspective view of components of one embodiment of a spinal implant system in accordance with the principles of the present disclosure disposed with vertebrae.

End face 108 is connected with a mating element 124. Mating element 124 includes a head 126 configured for disposal with cavity 68. Mating element 124 includes a cylindrical shaft extending from head 126 that includes a thread form, which is engaged with end face 108 in threaded fixation. Mating element 124 is configured to facilitate alignment with endplate 60 such that head 126 is aligned with the opening of cavity 68. Implant 100 translates into cavity 68 by guiding head 126 along the surfaces of ramp 70 into cavity 68, as described herein. Disposal of mating element 124 with cavity 68 and engagement of head 126 with the surfaces of wall 66 that define cavity 68 form a spheroidal joint 128, as shown in FIG. 15. In some embodiments, head 126 comprises a ball and cavity 68 comprises a socket such that spheroidal joint 128 includes a ball and socket configuration. In some embodiments, the mating elements can include biasing members, clips, key/keyway/keyslot, dovetail, tongue/groove, male/female, pin/groove, threaded, barbs, hooks and/or adhesive. In some embodiments, the mating elements are machined with end face 108 to limit a length of spinal construct 12.

In some embodiments, spheroidal joint 128 facilitates movement of implant 100 relative to endplate 60 in a plurality of degrees of freedom to one or a plurality of orientations. In some embodiments, spheroidal joint 128 facilitates movement of implant 100 relative to endplate 60 between a first angular orientation and a second angular orientation. In some embodiments, spheroidal joint 128 provides rotation of implant 100 about axis X1 relative to endplate 60 and disposal of implant 100 at a plurality of orientations relative endplate 60.

Body 130 has a tubular configuration and is oriented for disposal within axial cavity 114. Body 130 extends in a linear configuration relative to axis X1. In some embodiments, body 130 may extend in alternate configurations, such as, for example, arcuate, offset, staggered and/or angled portions, which may include acute, perpendicular and obtuse.

Body 130 extends between an end 132 and an end 134. End 132 defines an end face 136 configured to engage endplate 14, as described herein. In some embodiments, end face 136 can include a surface that may be rough, textured, porous, semi-porous, dimpled and/or polished.

Body 130 includes a wall, such as, for example, a tubular wall 138. In some embodiments, wall 138 includes a cylindrical cross-section. In some embodiments, the cross-sectional geometry of wall 138 may have various configurations, such as, for example, round, oval, oblong, triangular, polygonal having planar or arcuate side portions, irregular, uniform, non-uniform, consistent, variable, horseshoe shape, U-shape or kidney bean shape.

Wall 138 includes a surface 140. Surface 140 includes a gear rack 142 having a plurality of teeth 144 that are disposed therealong. Teeth 144 extend into opening 120 for engagement of a surgical instrument with rack 142 to facilitate axial translation of body 130 relative to body 102 between a contracted configuration and an expanded configuration for disposal in a selected orientation, as described herein. In some embodiments, teeth 144 are disposed in a linear, serial configuration along surface 140 in an offset configuration relative to axis X1. In some embodiments, the offset configuration of teeth 144 cause teeth 144 to extend into opening 120 to facilitate axial translation of body 130 relative to body 102 between a contracted configuration and an expanded configuration for disposal in a selected orientation.

Wall 138 includes a surface 146 that defines an opening, such as, for example, an axial slot 148. Slot 148 is disposed along axis X1. Slot 148 is configured for engagement with a lock 150, as described herein. In some embodiments, the cross-sectional geometry of slot 148 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 146 is smooth, even, rough, textured, porous, semi-porous, dimpled and/or polished. In some embodiments, slot 148 may extend in alternate configurations, such as, for example, arcuate, offset, staggered and/or angled portions, which may include acute, perpendicular and obtuse relative to axis X1.

End face 136 is connected with a mating element 152. Mating element 152 includes a head 154 configured for disposal with cavity 22. Mating element 152 includes a cylindrical shaft extending from head 154 that includes a thread form, which is engaged with end face 136 in threaded fixation. Mating element 152 is configured to facilitate alignment with endplate 14 such that head 154 is aligned with the opening of cavity 22. Implant 100 translates into cavity 22 by guiding head 154 along the surfaces of ramp 24 into cavity 22, as described herein. Disposal of mating element 152 with cavity 22 and engagement of head 154 with the surfaces of wall 20 that define cavity 22 form a spheroidal joint 156, as shown in FIG. 15. In some embodiments, head 154 comprises a ball and cavity 22 comprises a socket such that spheroidal joint 156 includes a ball and socket configuration. In some embodiments, the mating elements are machined with end face 136 to limit a length of spinal construct 12.

In some embodiments, spheroidal joint 156 facilitates movement of implant 100 relative to endplate 14 in a plurality of degrees of freedom to one or a plurality of orientations. In some embodiments, spheroidal joint 156 facilitates movement of implant 100 relative to endplate 14 between a first angular orientation and a second angular orientation. In some embodiments, spheroidal joint 156 provides rotation of implant 100 about axis X1 relative to endplate 14 and disposal of implant 100 at a plurality of orientations relative endplate 14.

Lock 150 includes a reduced diameter portion that is frangibly connected to a portion of lock 150. In some embodiments, lock 150 is fabricated from a fracturing and/or frangible material such that manipulation of a portion of lock 150 can fracture and separate a portion of lock 150 at a predetermined force and/or torque limit, as described herein. In some embodiments, as force and/or torque is applied and resistance increases, for example, the predetermined torque and force limit is approached. In some embodiments, lock 150 is configured for a threaded engagement with slot 148.

In some embodiments, a portion of lock 150 can fracture and separate at a predetermined force or torque limit, which may be in a range of approximately 2 Newton meter (N-m) to 8 N-m. In some embodiments, lock 150 may have the same or alternate cross section configurations, may be fabricated from a homogenous material or heterogeneously fabricated from different materials, and/or alternately formed of a material having a greater degree, characteristic or attribute of plastic deformability, frangible property and/ or break away quality to facilitate fracture and separation of lock 150.

In some embodiments, as shown in FIGS. 10-20, spinal implant system 10, as described herein, includes a provisional frame 160 that is configured for connection with one or more vertebral surfaces and/or one or more implants and spinal constructs, for example, to provisionally fix and/or stabilize endplates and/or a centerpiece implant with one or more vertebral surfaces. In some embodiments, provisional frame 160 can be employed as provisional and/or working construct and/or scaffold to temporarily support endplates and/or a centerpiece implant with one or more vertebral surfaces during a surgical treatment and/or provide a template configuration for spinal implants, as described herein. In some embodiments, spinal implant system 10 may include one or a plurality of provisional frames 160. In some embodiments, a plurality of provisional frames 160 may be disposed in various alternate orientations, such as, for example, side by side, parallel, transverse, co-axial and/or may be offset or staggered. In some embodiments, one or more components of provisional frame 60 may provide a template configuration for spinal implants, such as, implantable, final, permanent, removable, non-removable, bio-absorbable, resorbable and/or bio-degradable.

Figure 3:
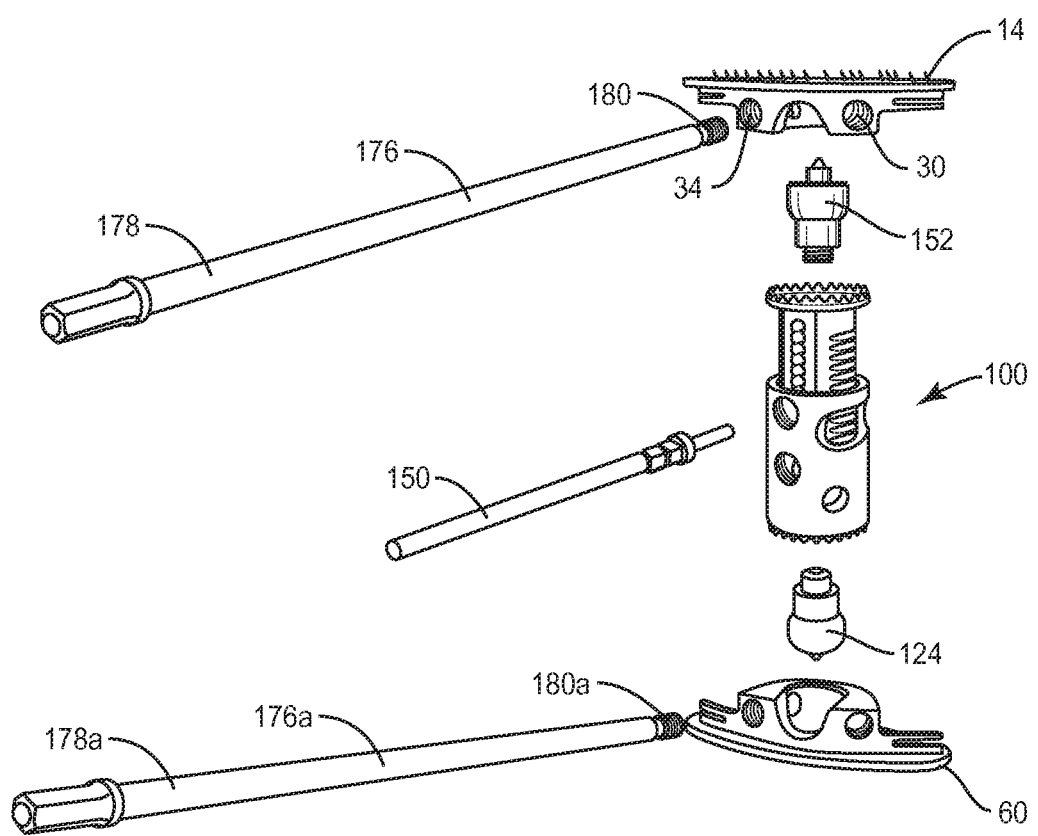
FIG. 3 is a perspective view of components of one embodiment of a spinal implant system in accordance with the principles of the present disclosure with parts separated.
Figure 4:
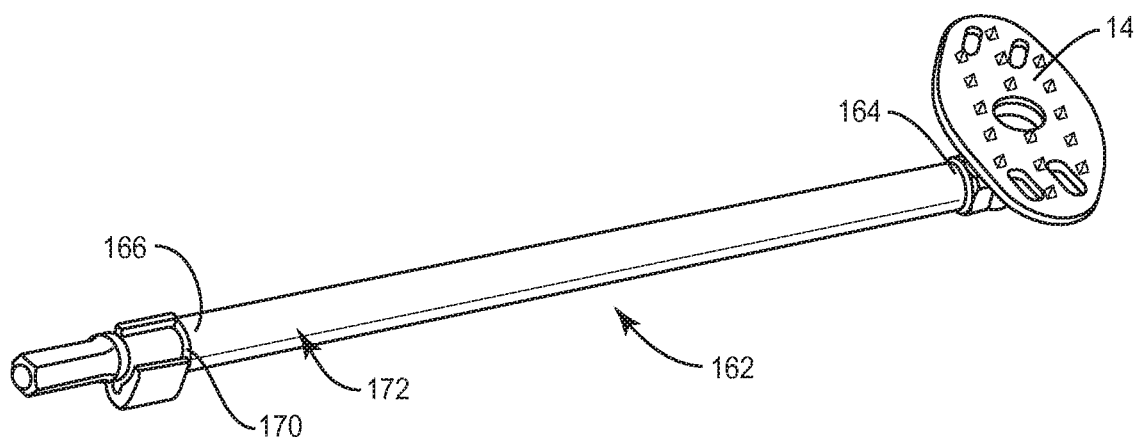
FIG. 4 is a perspective view of components of one embodiment of a spinal implant system in accordance with the principles of the present disclosure.
Figure 5:
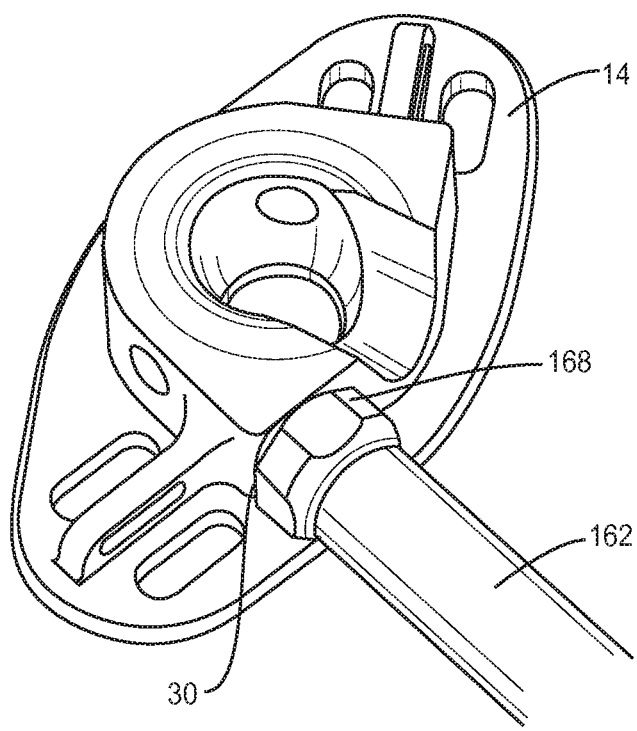
FIG. 5 is a break away view of the components shown in FIG. 4.
Figure 6:
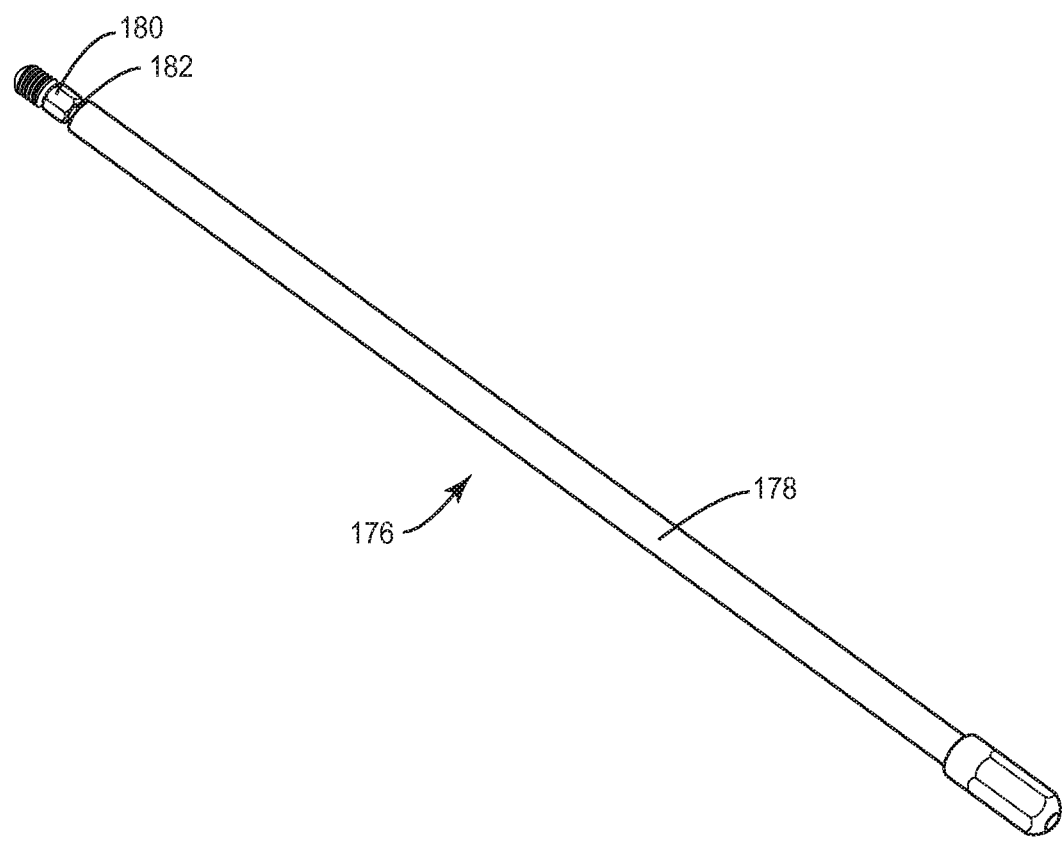
FIG. 6 is a perspective view of components of one embodiment of a spinal implant system in accordance with the principles of the present disclosure.

In some embodiments, provisional frame 160 includes inserter support 162, as shown in FIGS. 4 and 5. Inserter support 162 extends between an end 164 and an end 166. End 164 includes a threaded surface 168. Surface 168 is configured for engagement with opening 30 and/or opening 34 to facilitate insertion of end plate 14 and provisional fixation of endplate 14 with a selected vertebral surface. Inserter support 162 includes a surface 170 that defines a channel 172 extending between end 164 and end 166. Channel 172 is configured for disposal of a lock, such as, for example, a breakoff set screw 176, as shown in FIGS. 3 and 6.

Setscrew 176 includes a portion 178 and a portion 180. Portions 178, 180 are connected at a reduced diameter portion 182 that is frangibly connected to portion 180. In some embodiments, portion 180 is configured for engagement with opening 30 and/or opening 34. In some embodiments, portions 178, 180 are fabricated from a fracturing and/or frangible material such that manipulation of portion 178 relative to portion 180 can fracture and separate portion 178 from portion 180 at a predetermined force and/or torque limit, as described herein. In some embodiments, as force and/or torque is applied to portion 178 and resistance increases, for example, due to fixation of portion 180 with spinal construct 12, as described herein, the predetermined torque and force limit is approached.

In some embodiments, as shown in FIGS. 11-20, provisional frame 160 includes one or a plurality of stabilizers, such as, for example, rods 200. Rod 200 includes a collar that defines a cavity 202 configured for disposal of inserter support 162, as described herein. In some embodiments, provisional frame 160 may include a plurality of supports and/or stabilizers, which may be relatively disposed in a side by side, irregular, uniform, non-uniform, offset and/or staggered orientation or arrangement. In some embodiments, the supports and/or stabilizers can have a uniform thickness/diameter. In some embodiments, the supports and/or stabilizers may have various surface configurations, such as, for example, rough, threaded for connection with surgical instruments, arcuate, undulating, dimpled, polished and/or textured. In some embodiments, the thickness defined by the supports and/or stabilizers may be uniformly increasing or decreasing, or have alternate diameter dimensions along its length. In some embodiments, the supports and/or stabilizers may have various cross section configurations, such as, for example, oval, oblong, triangular, rectangular, square, polygonal, irregular, uniform, non-uniform, variable and/or tapered. In some embodiments, the supports and/or stabilizers may have various lengths.

In some embodiments, the supports and/or stabilizers may have a flexible configuration and fabricated from materials, such as, for example, polyester, polyethylene, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of the supports and/or stabilizers includes movement in a lateral or side to side direction and prevents expanding and/or extension in an axial direction. In some embodiments, all or only a portion of the supports and/or stabilizers may have a semi-rigid, rigid or elastic configuration, and/or have elastic properties, such as the elastic properties corresponding to the material examples described above. In some embodiments, the supports and/or stabilizers may be compressible in an axial direction.

Figure 7:
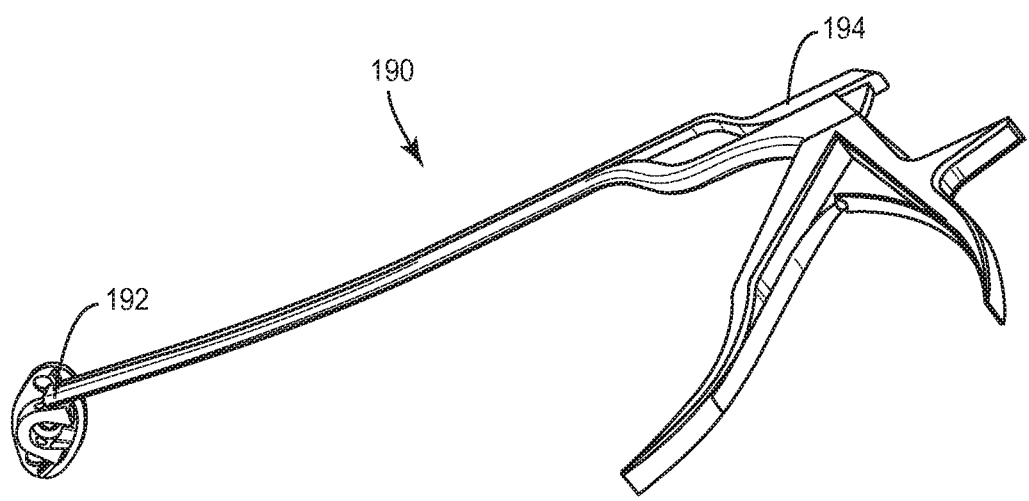
FIG. 7 is a perspective view of components of one embodiment of a spinal implant system in accordance with the principles of the present disclosure.
Figure 8:
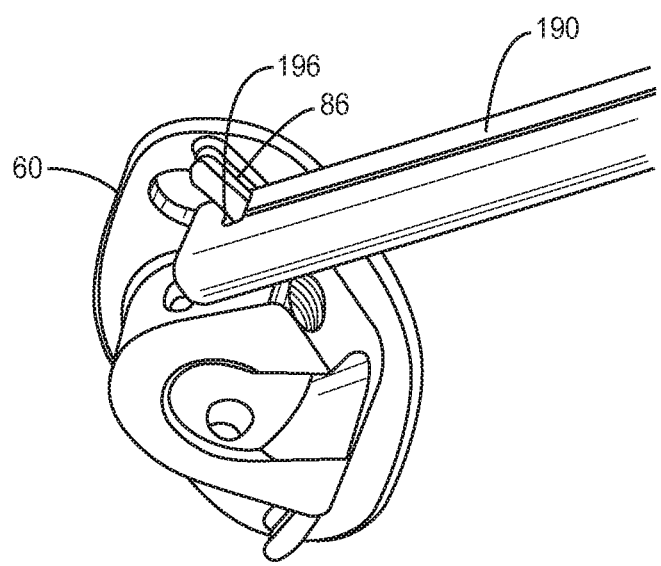
FIG. 8 is a break away view of the components shown in FIG. 7.

In some embodiments, as shown in FIGS. 7 and 8, spinal implant system 10, as described herein, includes an inserter 190, which is engageable with endplate 60 and/or endplate 14 for disposal with one or more vertebral surfaces. In some embodiments, inserter 190 is configured as a Kerrison type surgical instrument. Inserter 190 extends between an end 192 and an end 194. End 192 includes a flange, such as, for example, a hook 196 that is configured for engagement with groove 44 and/or groove 86 to facilitate insertion of endplate 60 below a superior nerve root.

Referring to FIGS. 9-23, in assembly, operation and use, spinal implant system 10, similar to the systems and methods described herein, and including spinal construct 12 is employed with a surgical procedure, such as, for example, a lumbar corpectomy for treatment of a spine of a patient including vertebrae V. Spinal implant system 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including vertebral replacement devices, interbody devices, plates, rods, and bone engaging fasteners for securement of the components of spinal construct 12.

Spinal implant system 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes vertebra V1 and vertebra V2. A diseased and/or damaged vertebra and intervertebral discs are disposed between the vertebrae V1 and V2. In some embodiments, spinal construct 12 is configured for insertion within a vertebral space S to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from vertebral surface E1 of vertebra V1 and/or vertebral surface E2 of vertebra V2. Spinal construct 12 is provided with at least one agent, similar to those described herein, to promote new bone growth and fusion to treat the affected section of vertebrae V. The components of spinal implant system 10 may be completely or partially revised, removed or replaced. In some embodiments, spinal construct 12 is employed to stabilize vertebrae V as a pre-assembled device or can be assembled in situ.

Figure 9:
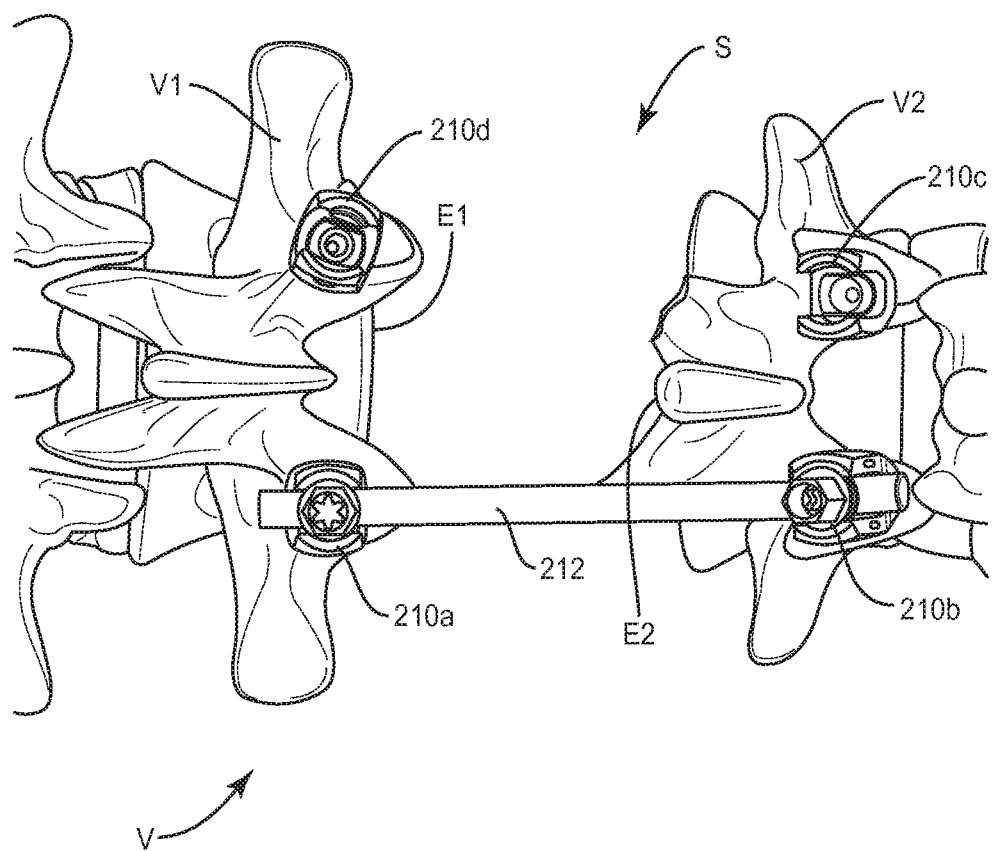
FIG. 9 is a plan view of components of one embodiment of a spinal implant system in accordance with the principles of the present disclosure disposed with vertebrae.

Pilot holes are made in selected vertebrae V1, V2 for receiving fasteners, such as, for example, bone screws 210a, 210b, 210c, 210d. Bone screws 210a, 210b, 210c, 210d are delivered to the surgical site and implanted with vertebrae V such that each bone screw is inserted, attached or otherwise engaged with a particular vertebra, as shown in FIG. 9. Bone screws 210a, 210b, 210c, 210d each include a receiver defining an implant cavity configured for disposal of vertebral rods 212. Vertebral rod 212 is delivered to the surgical site and connected with bone screws 210a and 210b for implant with a lateral portion of vertebrae V in connection treating the spine disorder.

Figure 10:
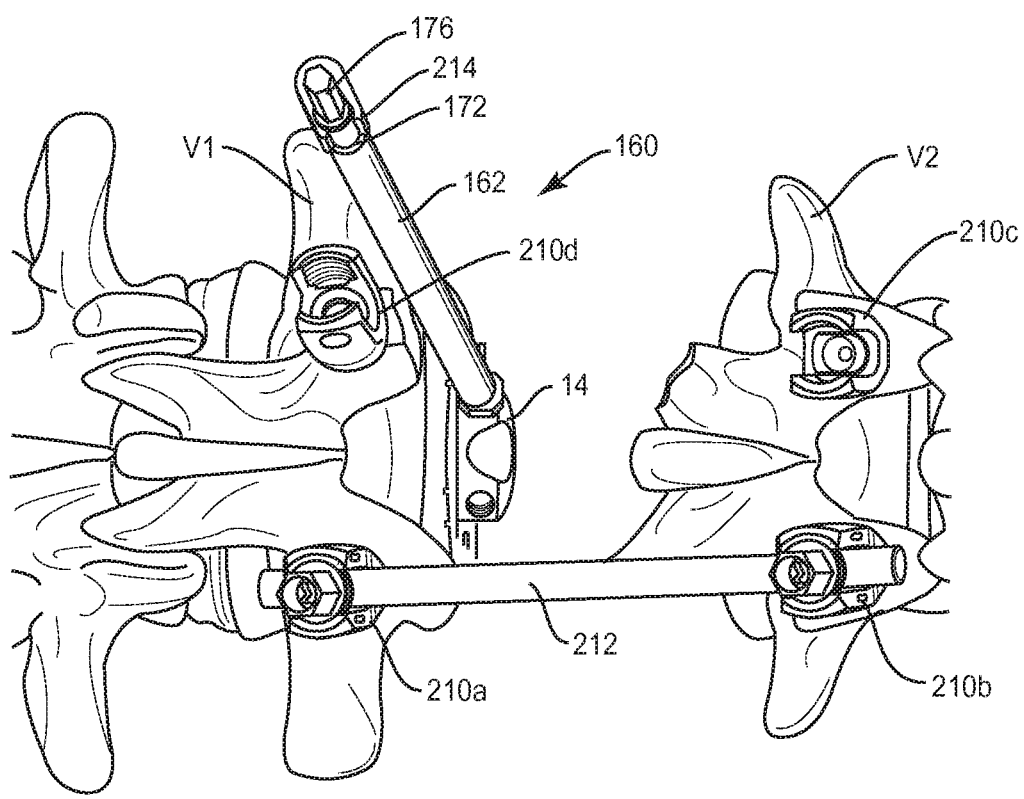
FIG. 10 is a plan view of components of one embodiment of a spinal implant system in accordance with the principles of the present disclosure disposed with vertebrae.

Endplate 14, as described herein, is connected with inserter support 162, which comprises a portion of provisional frame 160, via opening 30 such that inserter support 162 extends laterally from endplate 14, as shown in FIG. 10. Breakoff set screw 176 is disposed with channel 172. In some embodiments, a spacer 214 is engaged with break off set screw 176 and inserter support 162 to resist and/or prevent undesired engagement of portion 180 with endplate 14.

Figure 11:
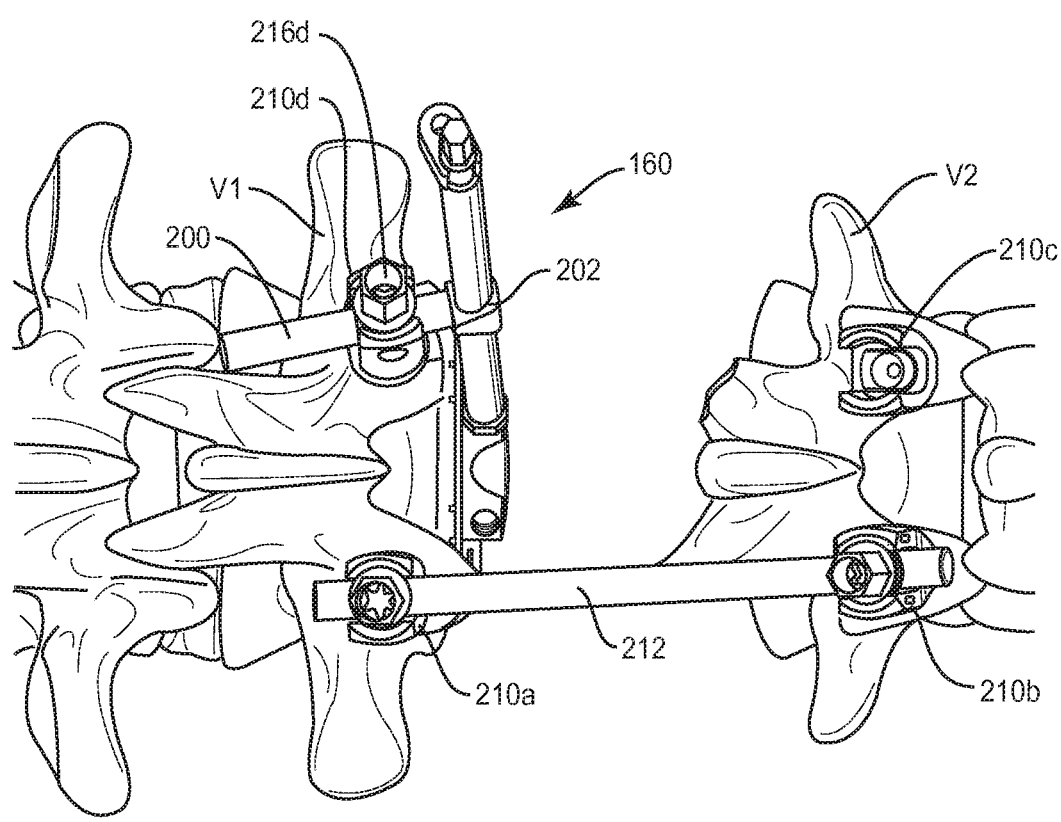
FIG. 11 is a plan view of components of one embodiment of a spinal implant system in accordance with the principles of the present disclosure disposed with vertebrae.

Endplate 14 is inserted into vertebral space S via a posterior approach for engagement with vertebral surface E1. In some embodiments, inserter support 162 is engaged with endplate 14 and inserted laterally to a dural sac of the spine and then rotated between vertebrae V1, V2 for positioning. In some embodiments, endplate 14 may be delivered to the surgical site with inserter 190, as described herein. Rod 200, as described herein, which comprises a portion of provisional frame 160, is connected with bone screw 210d with a coupling member, such as, for example, a setscrew 216d, as shown in FIG. 11. Inserter support 162 is disposed with cavity 202. Attachment of inserter support 162 with rod 200 provisionally fixes and/or stabilizes inserter support 162 and endplate 14 with vertebra V1.

Figure 12:
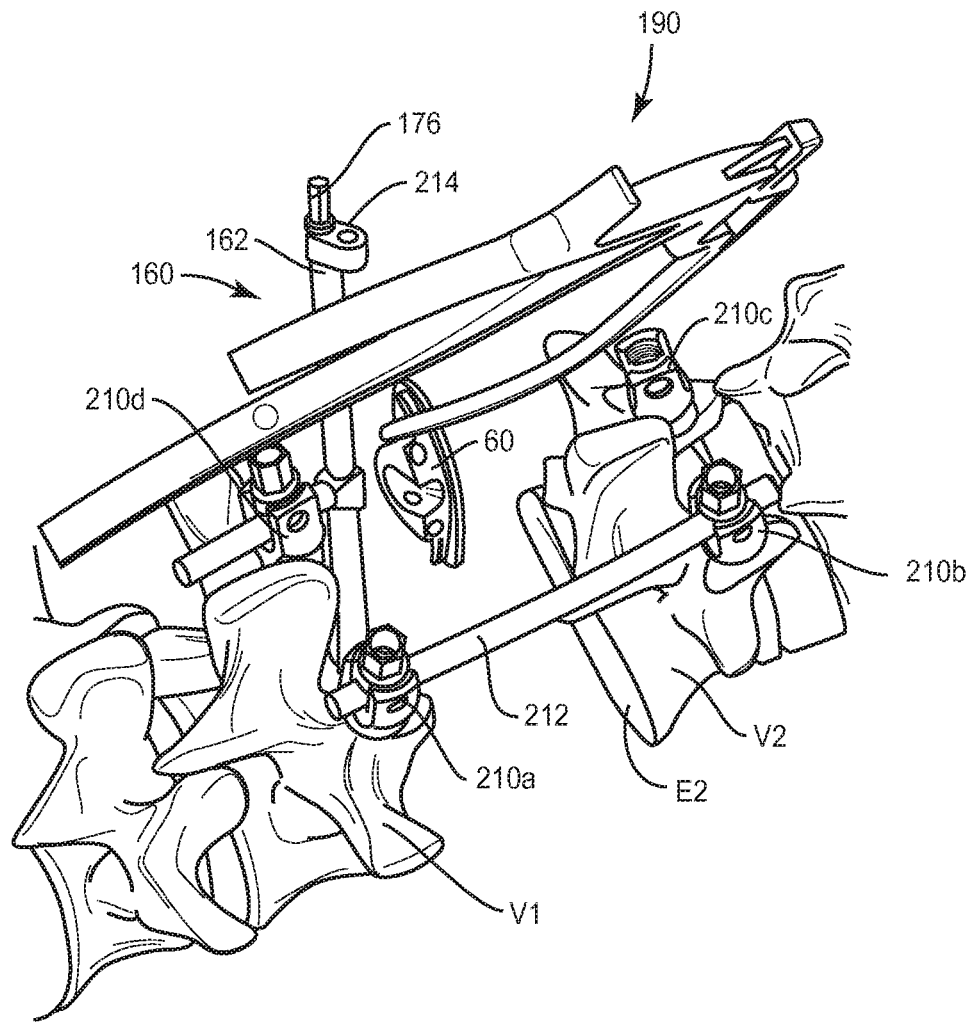
FIG. 12 is a perspective view of components of one embodiment of a spinal implant system in accordance with the principles of the present disclosure disposed with vertebrae.
Figure 13:
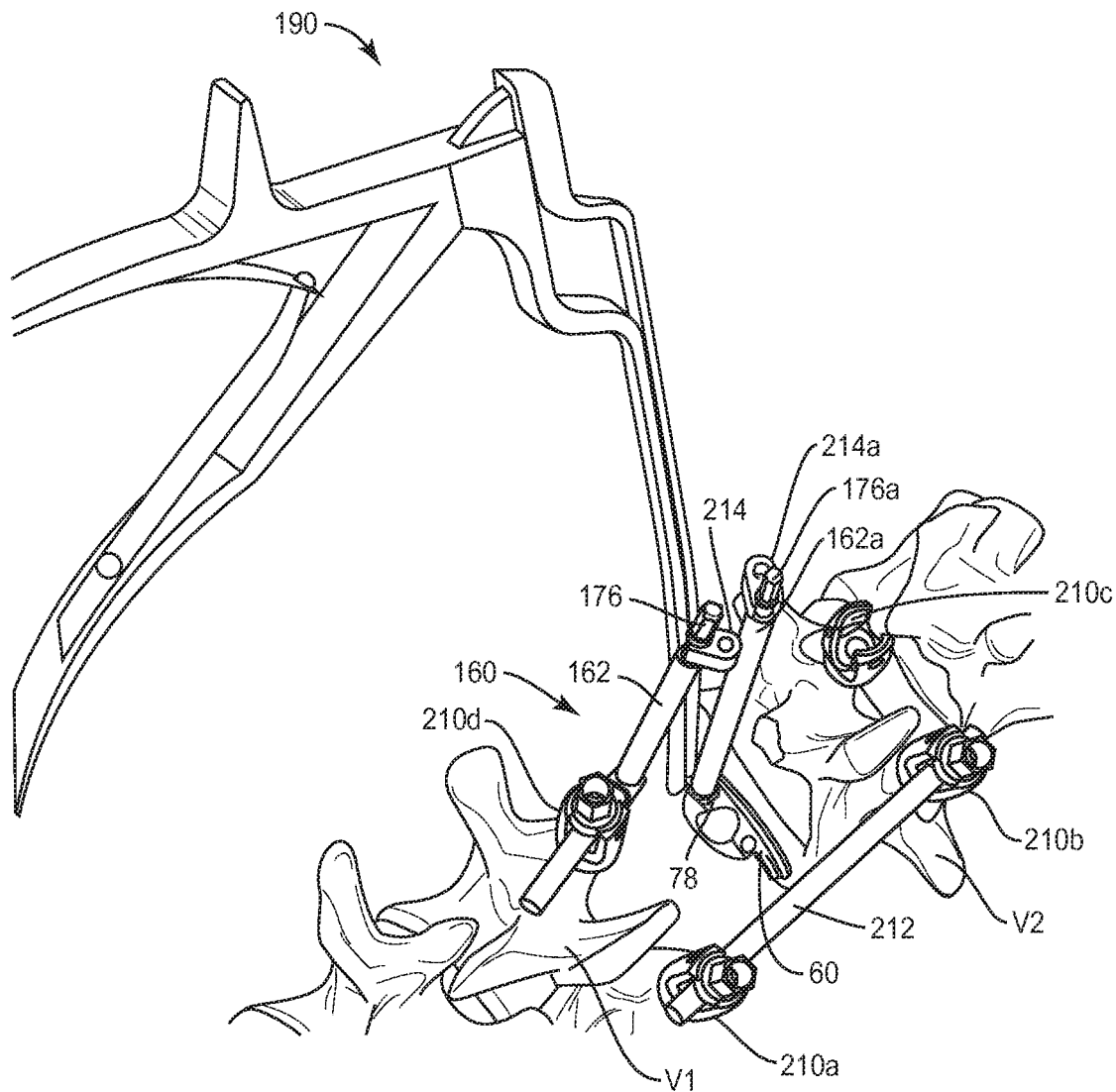
FIG. 13 is a perspective view of components of one embodiment of a spinal implant system in accordance with the principles of the present disclosure disposed with vertebrae.
Figure 14:
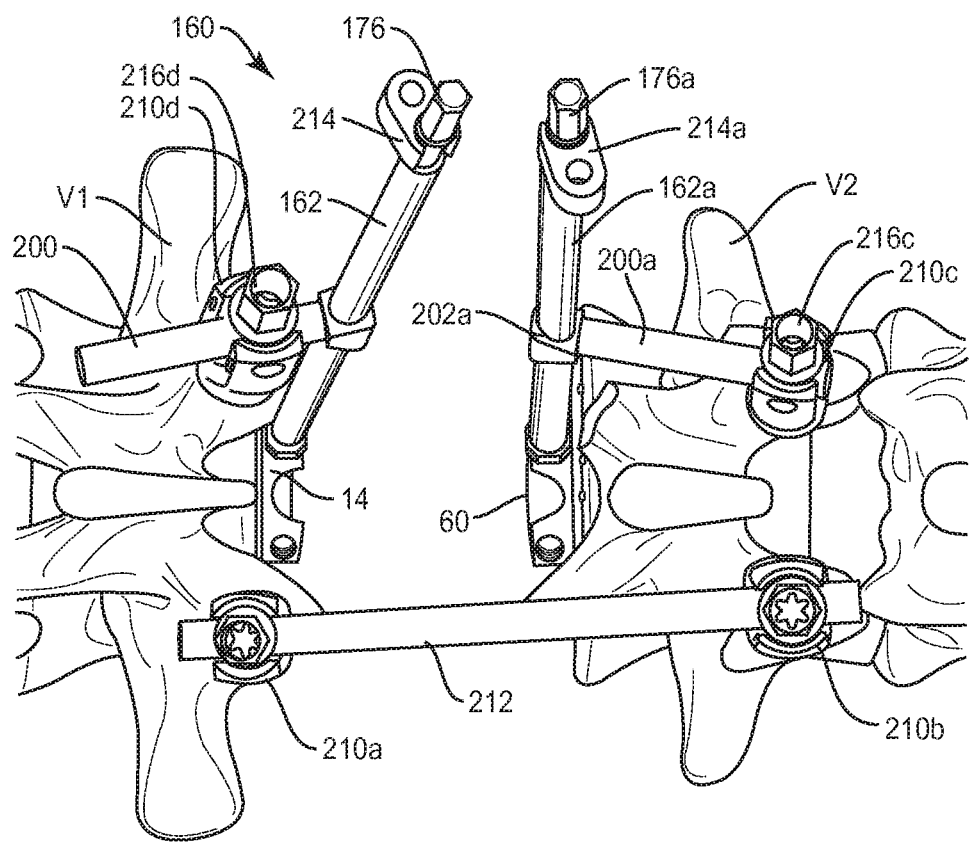
FIG. 14 is a plan view of components of one embodiment of a spinal implant system in accordance with the principles of the present disclosure disposed with vertebrae.

Endplate 60 is connected with inserter 190, as shown in FIGS. 12 and 13, via groove 80 or groove 86, as described herein, and inserted into vertebral space S via a posterior approach for engagement with vertebral surface E2. In some embodiments, endplate 60 is inserted below a superior nerve root of the spine. An inserter support 162a, similar to support 162, is connected with endplate 60 via opening 74. A breakoff set screw 176a is disposed with inserter support 162a. In some embodiments, a spacer 214a is engaged with break off set screw 176a and inserter support 162a to prevent and/or resist undesired engagement of breakoff set screw 176a with spinal construct 12. A rod 200a, similar to rod 200, which comprises a portion of provisional frame 160, is connected with bone screw 210c with a lock, such as, for example, a setscrew 216c, as shown in FIG. 14. Inserter support 162a is disposed with cavity 202a. Attachment of inserter support 162a with rod 200a provisionally fixes and/or stabilizes inserter support 162a and endplate 14 with vertebra V2.

Figure 16:
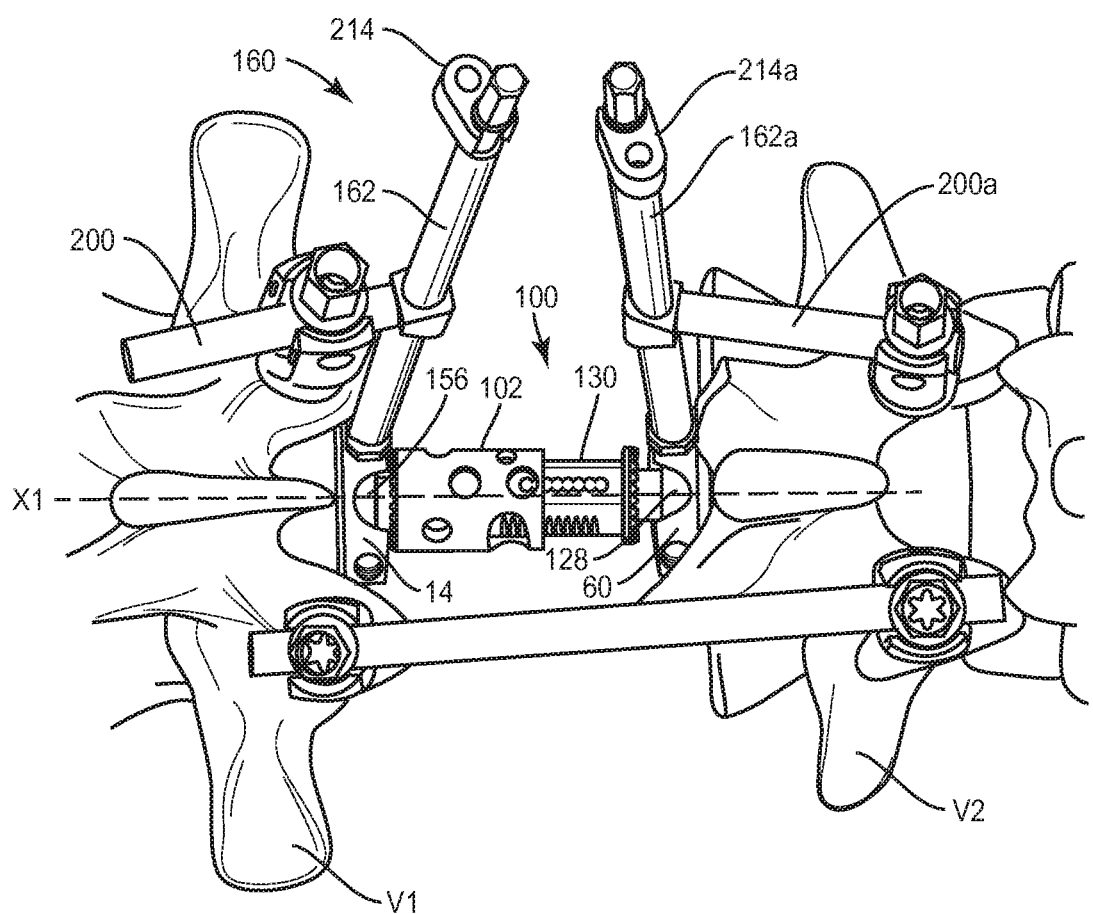
FIG. 16 is a plan view of components of one embodiment of a spinal implant system in accordance with the principles of the present disclosure disposed with vertebrae.

Implant 100, as described herein, is delivered to the surgical site via a posterior approach and inserted into vertebral space S, as shown in FIGS. 15 and 16. Implant 100 is delivered adjacent the components of spinal construct 12 and inserted with endplates 14, 60. Mating element 124 is aligned with endplate 60 such that head 126 is aligned with the opening of cavity 68. Implant 100 translates into cavity 68 by guiding head 126 along the surfaces of ramp 70 into cavity 68 for in-situ assembly of the components of spinal construct 12. Disposal of mating element 124 with cavity 68 and engagement of head 126 with the surfaces of wall 66 form spheroidal joint 128. Mating element 152 is aligned with endplate 14 such that head 154 is aligned with the opening of cavity 22. Implant 100 translates into cavity 22 by guiding head 154 along the surfaces of ramp 24 into cavity 22 for in-situ assembly of the components of spinal construct 12. Disposal of mating element 152 with cavity 22 and engagement of head 154 with the surfaces of wall 20 form spheroidal joint 156.

Figure 17:
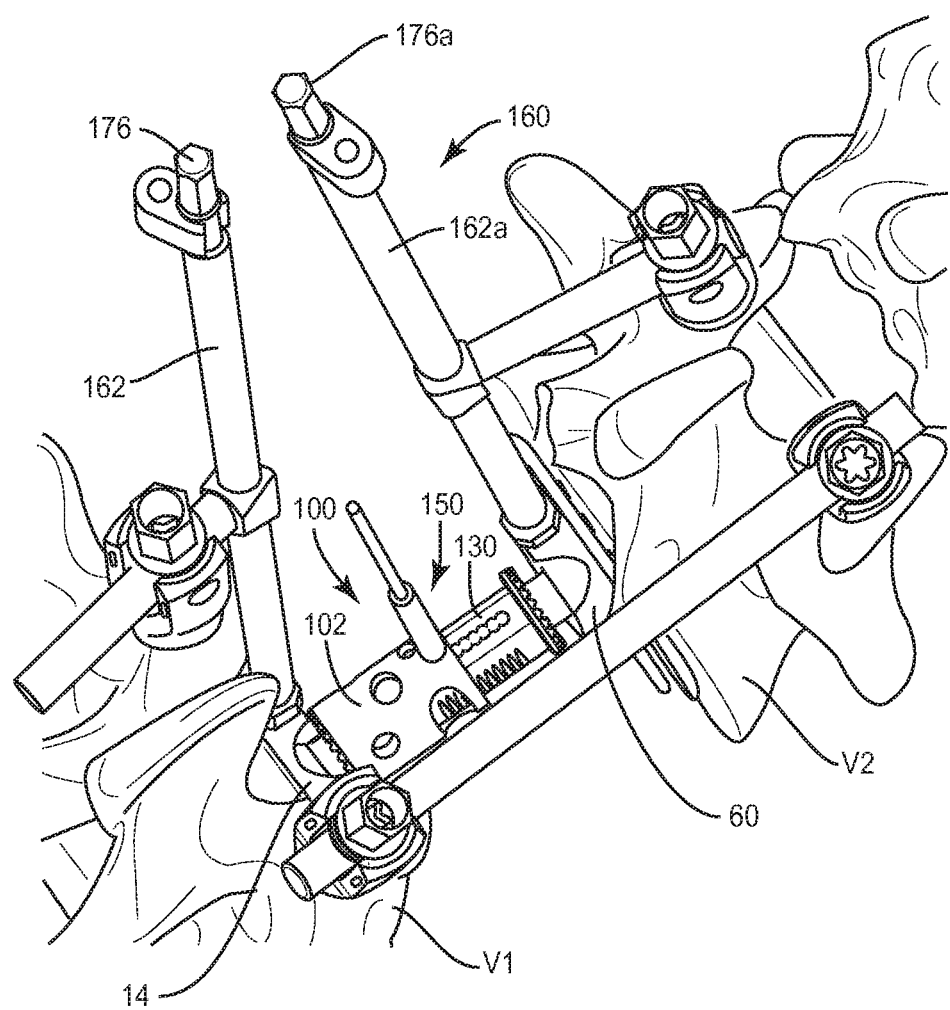
FIG. 17 is a perspective view of components of one embodiment of a spinal implant system in accordance with the principles of the present disclosure disposed with vertebrae.
Figure 18:
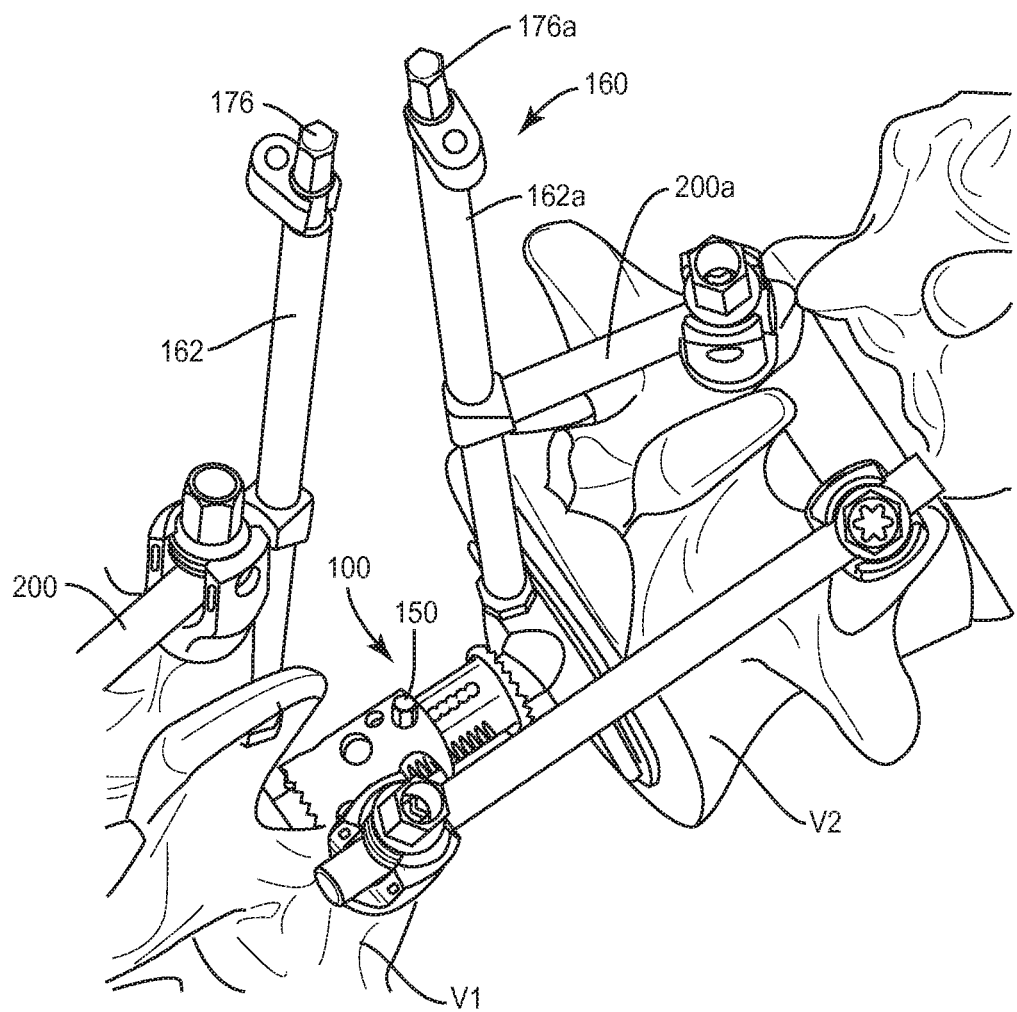
FIG. 18 is a perspective view of components of one embodiment of a spinal implant system in accordance with the principles of the present disclosure disposed with vertebrae.

An instrument (not shown) is configured to selectively expand and/or contract body 130 relative to body 102 of implant 100. Lock 150 is engaged with implant 100 to fix body 130 relative to body 102 at a selected expansion, as shown in FIG. 17. As a force and/or torque is applied to lock 150 and resistance increases, for example, the predetermined torque and force limit is approached, a portion of lock 150 fractures and separates at a predetermined force or torque limit, as shown in FIG. 18.

Figure 19:
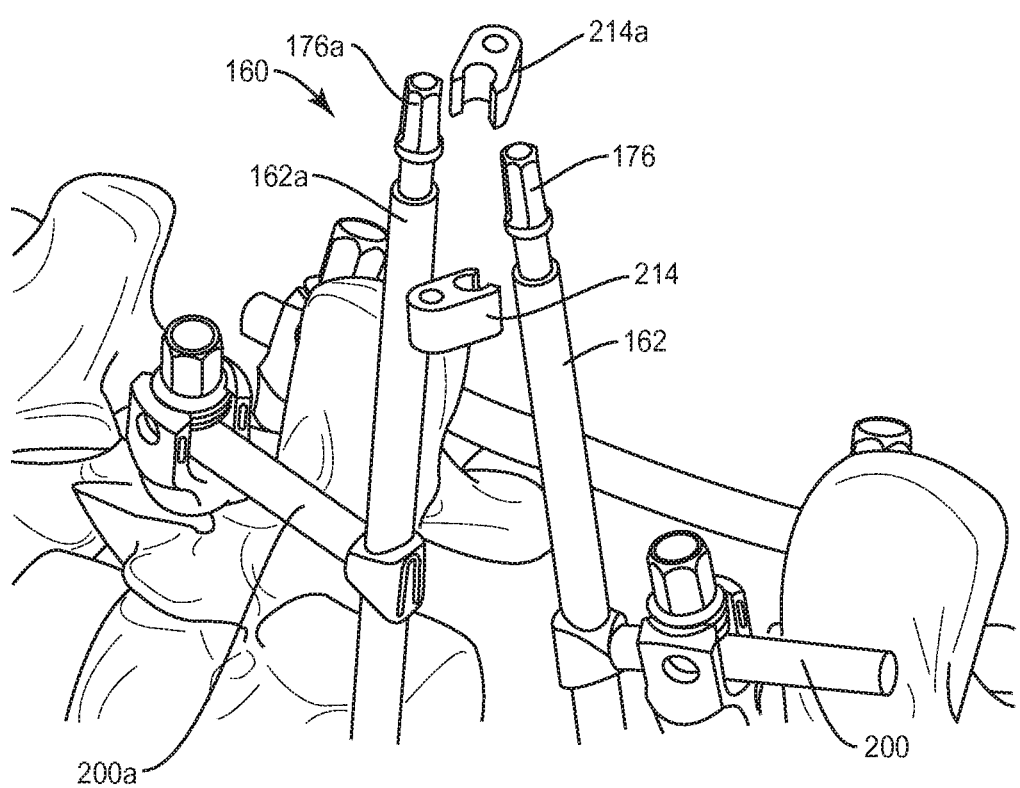
FIG. 19 is a perspective view of components of one embodiment of a spinal implant system in accordance with the principles of the present disclosure disposed with vertebrae.
Figure 20:
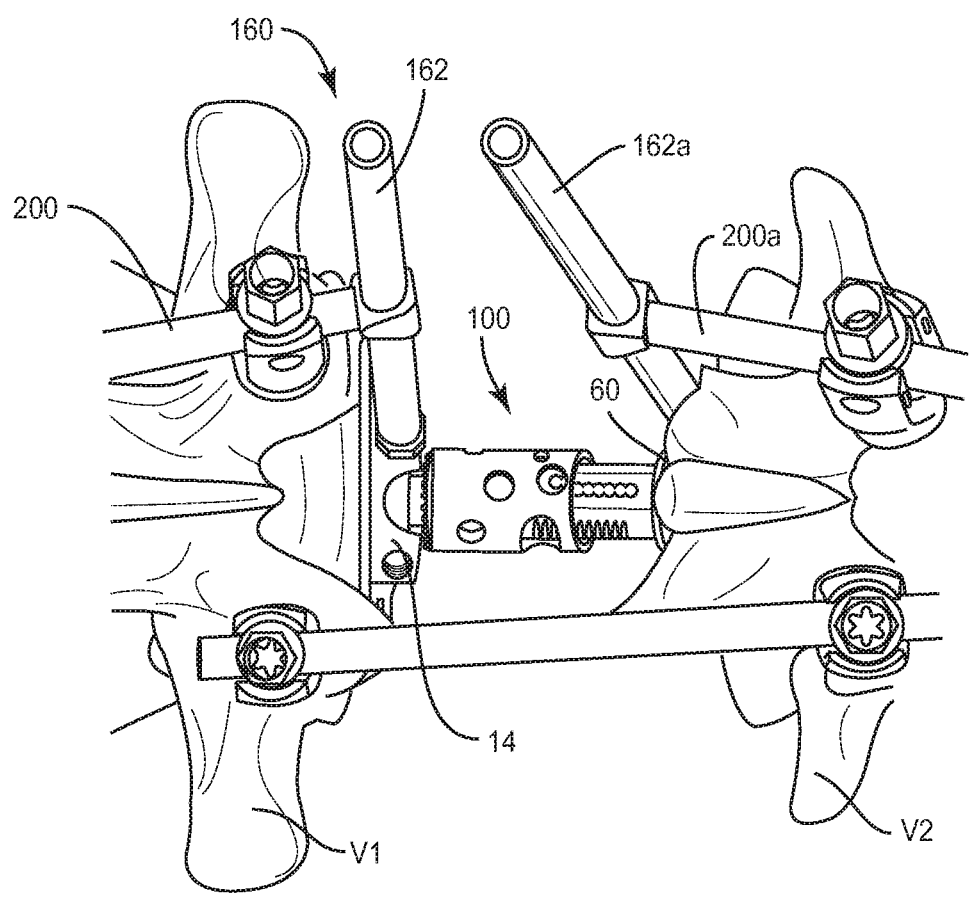
FIG. 20 is a plan view of components of one embodiment of a spinal implant system in accordance with the principles of the present disclosure disposed with vertebrae.
Figure 21:
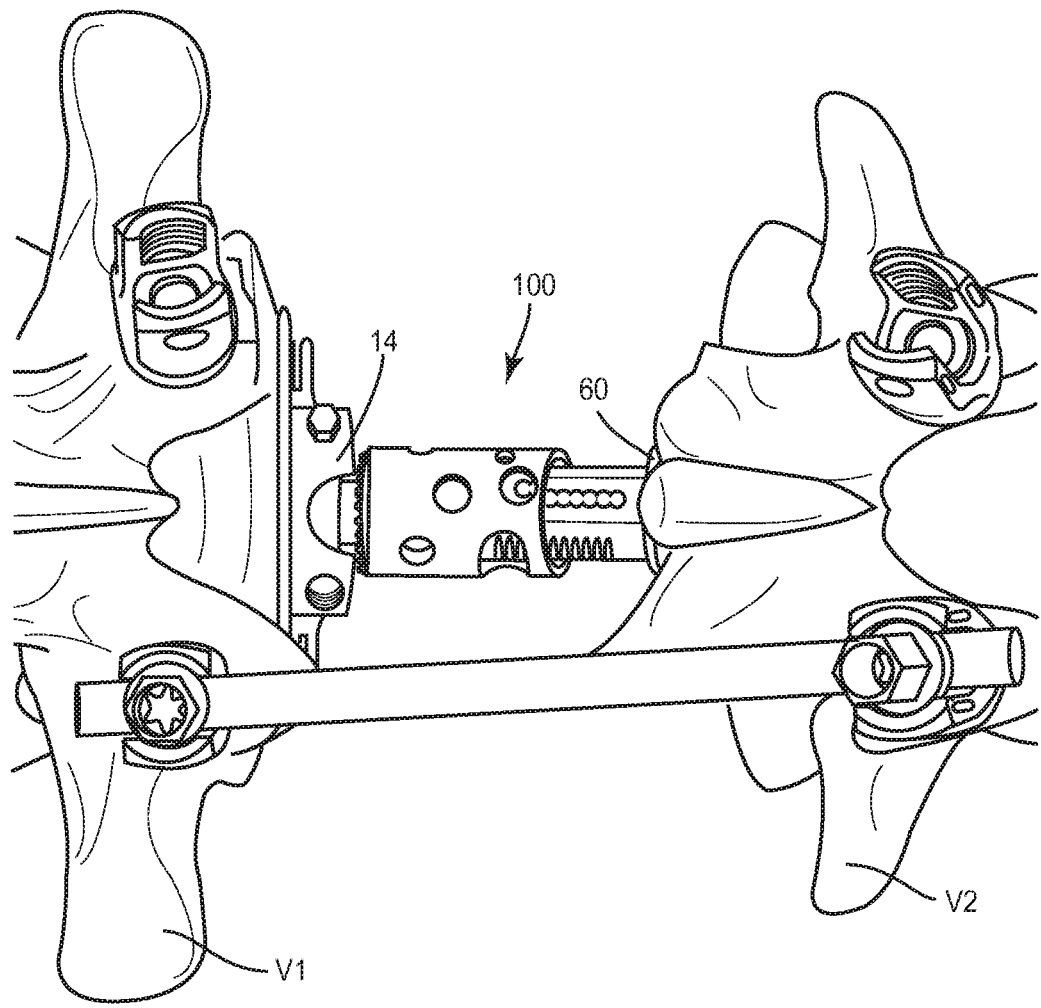
FIG. 21 is a plan view of components of one embodiment of a spinal implant system in accordance with the principles of the present disclosure disposed with vertebrae.
Figure 22:
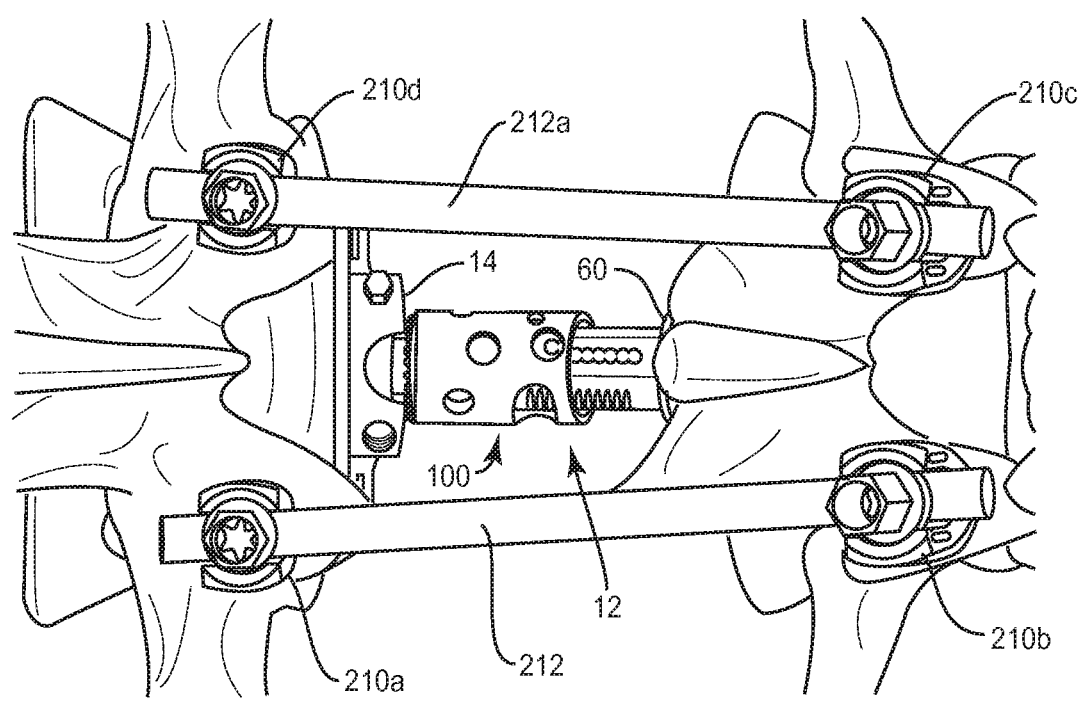
FIG. 22 is a plan view of components of one embodiment of a spinal implant system in accordance with the principles of the present disclosure disposed with vertebrae.
Figure 23:
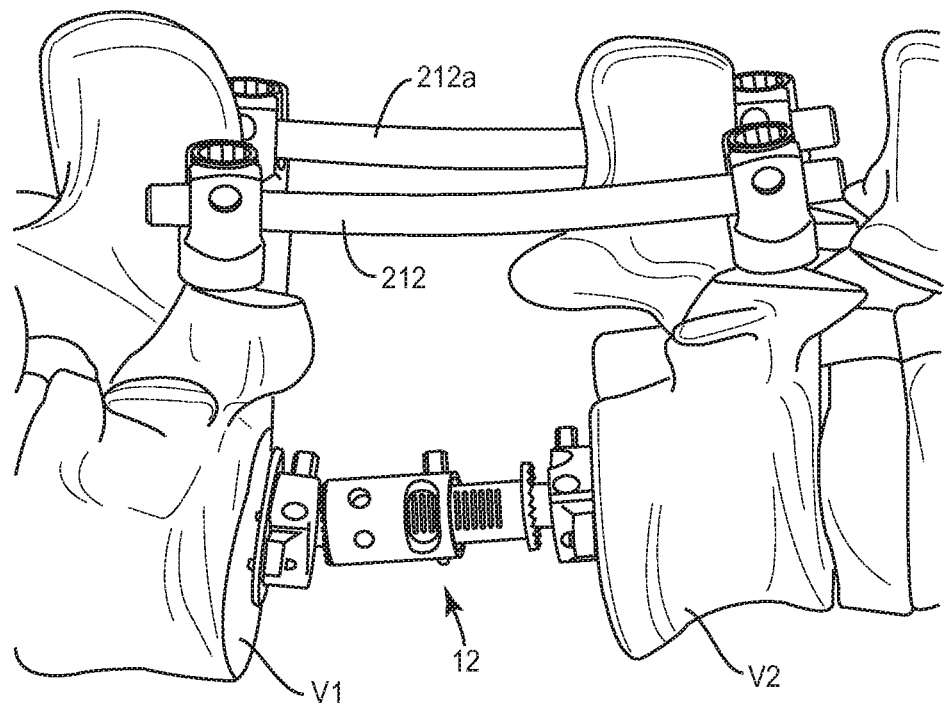
FIG. 23 is a perspective view of components of one embodiment of a spinal implant system in accordance with the principles of the present disclosure disposed with vertebrae.

Spacers 214, 214a are removed from inserters 162, 162a, as shown in FIG. 19. Breakoff set screws 176, 176a translate into engagement with endplates 14, 60. Breakoff set screws 176, 176a are manipulated such that portion 180 and a portion 180a fracture and separate from portion 178 and a portion 178a at a predetermined force and/or torque limit, as described herein. Portions 178, 178a are removed from inserters 162, 162a, as shown in FIG. 20. Inserters 162, 162a and rods 200, 200a are removed from vertebrae V, as shown in FIG. 21.

A vertebral rod 212a is delivered to the surgical site and connected with bone screws 210c and 210d for implant with a contralateral portion of vertebrae V in connection treating the spine disorder. In some embodiments, spinal construct 12 includes vertebral rod 212 and/or vertebral rod 212a. In some embodiments, an agent(s), as described herein, may be applied to areas of the surgical site to promote bone growth. In some embodiments, one or all of the components of spinal implant system 10 can be delivered to the surgical site via mechanical manipulation and/or a free hand technique.

In some embodiments, spinal construct 12 may include fastening elements, which may include locking structure, configured for fixation with vertebrae to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 10 can be used with screws to enhance fixation. In some embodiments, spinal implant system 10 and any screws and attachments may be coated with an agent, similar to those described herein, for enhanced bony fixation to a treated area. The components of spinal implant system 10 can be made of radiolucent materials such as polymers. Radiomarkers may be included for identification under x-ray, fluoroscopy, CT or other imaging techniques.

In some embodiments, the use of microsurgical and image guided technologies may be employed to access, view and repair spinal deterioration or damage, with the aid of spinal implant system 10. Upon completion of the procedure, the non-implanted components, surgical instruments and assemblies of spinal implant system 10 are removed and the incision is closed.

Figure 24:
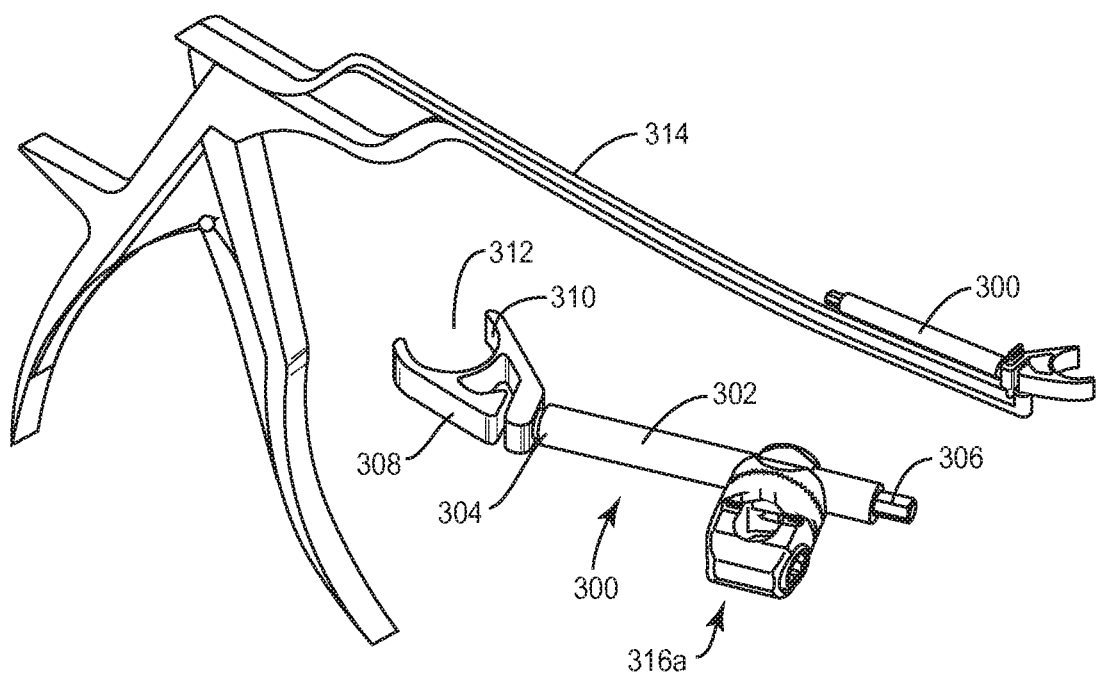
FIG. 24 is a perspective view of components of one embodiment of a spinal implant system in accordance with the principles of the present disclosure.
Figure 25:
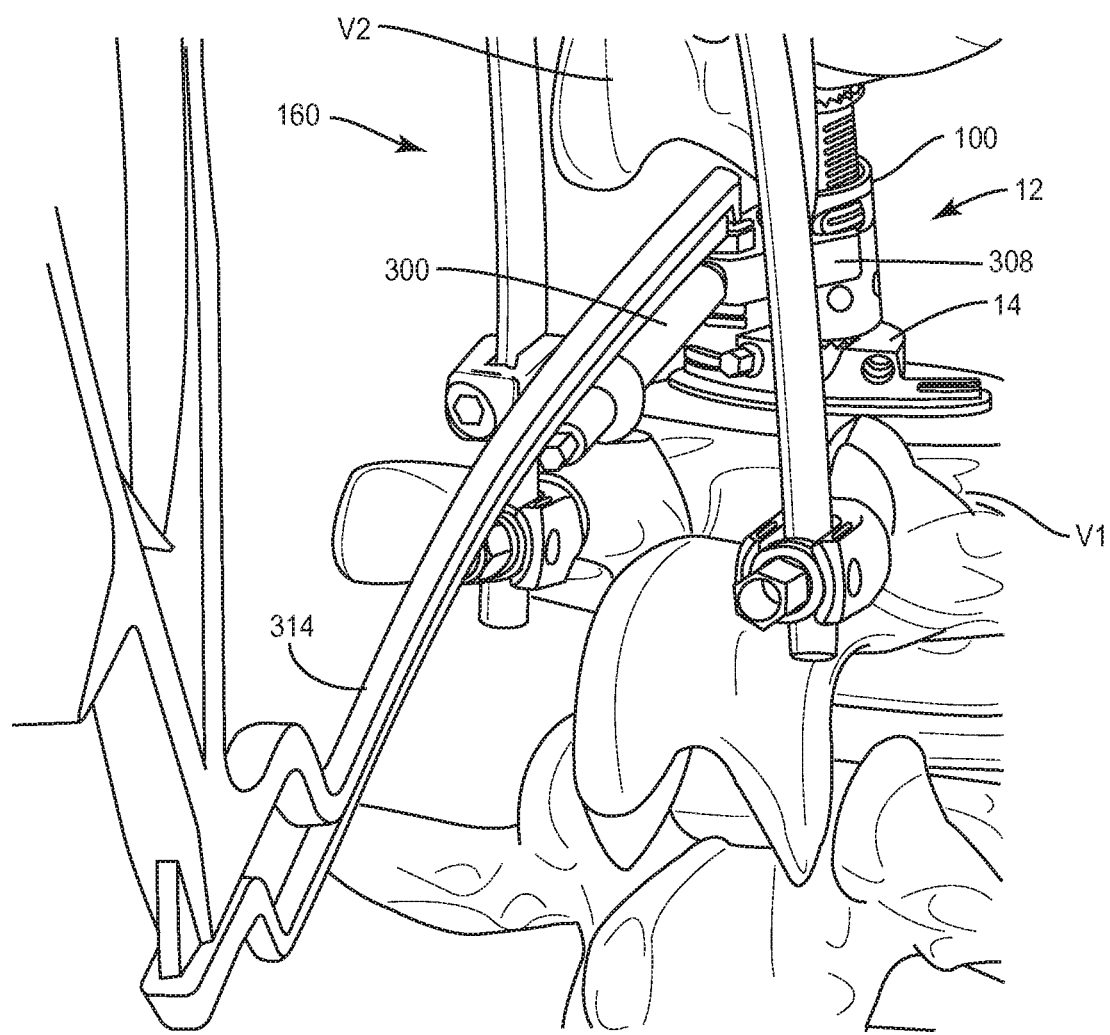
FIG. 25 is a perspective view of components of one embodiment of a spinal implant system in accordance with the principles of the present disclosure disposed with vertebrae.
Figure 26:
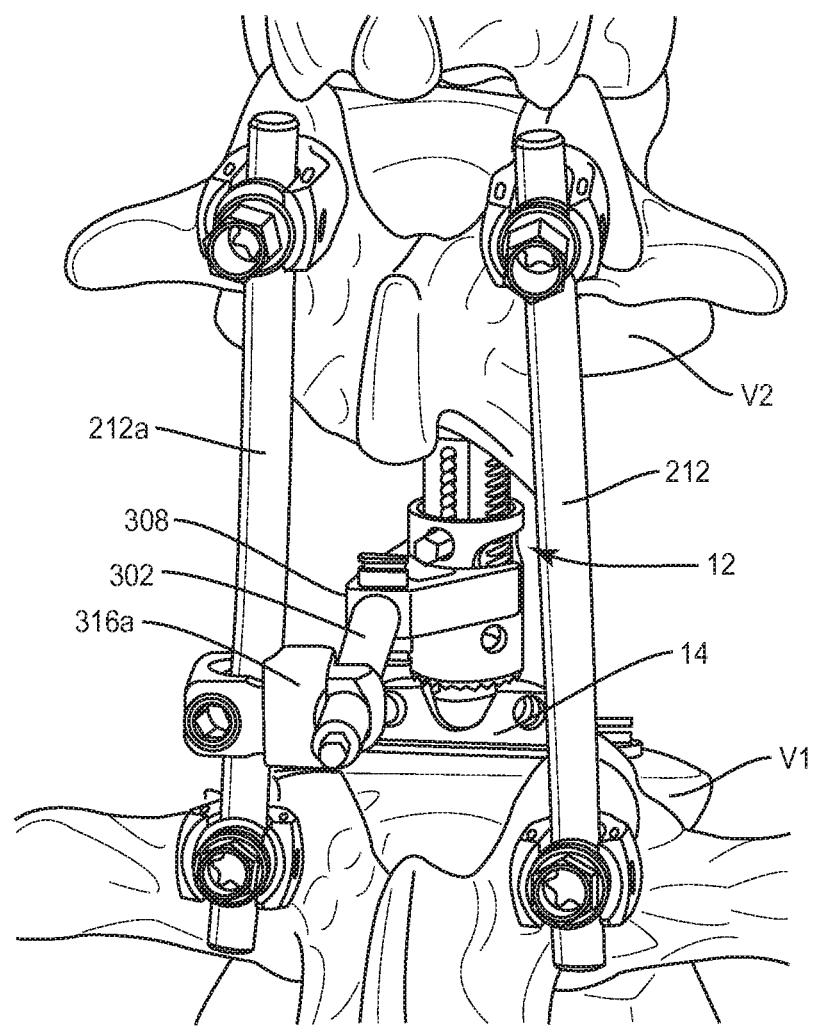
FIG. 26 is a plan view of components of one embodiment of a spinal implant system in accordance with the principles of the present disclosure disposed with vertebrae.

In one embodiment, as shown in FIGS. 24-26, spinal implant system 10, similar to the systems and methods described herein, includes spinal construct 12, similar to that described herein. Spinal construct 12 is employed with provisional frame 160, similar to that described herein, which includes a posterior fixator 300 that is connected with an existing VBR device such as spinal construct 12, as described with regard to FIGS. 1-23, for positional locking of implant 100 with one or more components of spinal construct 12.

Fixator 300 includes a shaft 302 that extends between an end 304 and an end 306. End 304 includes a gripping portion, such as, for example, a clip 308. Clip 308 includes a surface 310 that defines a cavity 312. In some embodiments, clip 308 is configured for releasable engagement with implant 100. In some embodiments, clip 308 is configured for permanent engagement with implant 100. In some embodiments, clip 308 is configured for engagement with implant 100 and movable relative thereto via slidable engagement therewith, for example, in relative circumferential rotation. In some embodiments, clip 308 includes a resilient configuration configured to snap fit with implant 100.

Fixator 300 is configured for attachment to one or more components of spinal construct 12, such as, for example, a vertebral rod 212a and implant 100. Vertebral rod 212a is attached with vertebrae V1, V2, as described herein. Fixator 300 is connected or attached with vertebral rod 212a via a connector 316a to positionally fix and/or stabilize implant 100 with the components of spinal construct 12.

In some embodiments, connector 316a is selectively adjustable and/or rotatable to movably adjust fixator 300 relative to vertebral rod 212a and/or implant 100 for connecting fixator 300 with the components of spinal construct 12. In some embodiments, connector 316a includes radial splines that can be spaced apart for rotation of shaft 302 relative to vertebral rod 212a and engagement of the splines for selective fixation of shaft 302 in a particular orientation relative to vertebral rod 212a. In a fixed orientation of shaft 302 relative to vertebral rod 212a, fixator 300 stabilizes implant 100, which is connected with endplates 14, 60 and disposed with vertebrae V. In some embodiments, fixator 300 is locked with rod 212a to fix implant 100 with endplates 14, 60 and vertebrae V.

In some embodiments, fixator 300 is connected with a surgical instrument, such as, for example, an inserter 314, similar to those described herein, and as shown in FIG. 24, for manipulation thereof during surgical treatment, as described herein. Inserter 314 delivers fixator 300 to a surgical site with vertebrae V1, V2 adjacent the components of spinal construct 12.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
    an expandable member including an outer body and an inner body movably positioned within an axial cavity of the outer body, the inner body comprising spaced apart indentations that each extend perpendicular to a longitudinal axis defined by the axial cavity, the indentations being configured for engagement with a surgical instrument to facilitate axial translation of the inner body relative to the outer body;
    a plating element coupled to the expandable member;
    an endplate engageable with the mating element to connect the expandable member with the endplate; and
    a spinal rod attachable with vertebral surfaces and a support connected with the expandable member and the spinal rod.

2. A spinal construct as recited in claim 1, wherein the mating element comprises a head that is disposed within a cavity of the endplate such that engagement of the head with surfaces of the endplate that define the cavity forms a spheroidal joint.

3. A spinal construct as recited in claim 1, wherein the mating element comprises a head that is disposed within a cavity defined by a circumference of a wall of the endplate, the wall comprising a cutout that is in communication with the cavity.

4. A spinal construct as recited in claim 3, wherein the cutout has a U-shaped configuration.

5. A spinal construct as recited in claim 3, wherein wall includes threaded openings, the cutout being positioned between the threaded openings.

6. A spinal construct as recited in claim 1, wherein the mating element comprises a ball that is disposed within a socket of the endplate such that the ball and the socket define a ball and socket joint.

7. A spinal construct as recited in claim 1, wherein the mating element is removably coupled to the expandable member.

8. A spinal construct as recited in claim 1, wherein the mating element comprises a shaft having a thread form that engages with an end face of the outer body in threaded fixation.

9. A spinal construct as recited in claim 1, wherein the mating element comprises a shaft having a thread form that engages with an end face of the inner body in threaded fixation.

10. A spinal construct as recited in claim 1, wherein the outer body includes a window, at least one of the notches being viewable through the window.

11. A spinal construct as recited in claim 1, wherein the indentations are disposed in a linear, serial configuration along a continuously curved outer surface of the inner body.

12. A spinal construct as recited in claim 1, wherein the indentations extend into an outer surface of the inner body without extending through an opposite inner surface of the inner body.

13. A spinal construct as recited in claim 1, wherein the indentations extend about only a portion of a circumference of the inner body.

14. A spinal construct comprising:
    an expandable member including an outer body and an inner body movably positioned within an axial cavity of the outer body, the inner body comprising spaced apart indentations that each extend perpendicular to a longitudinal axis defined by the axial cavity, the indentations being configured for engagement with a surgical instrument to facilitate axial translation of the inner body relative to the outer body;

a first mating element coupled to the inner body;
a second mating element coupled to the outer body;
a first endplate engageable with the first mating element to connect the inner body with the first endplate;
a second endplate engageable with the second mating element to connect the outer body with the second endplate; and
a spinal rod attachable with vertebral surfaces and a support connected with the expandable member and the spinal rod.

15. A spinal construct as recited in claim 14, wherein:
the first mating element comprises a first head that is disposed within a first cavity of the first endplate such that engagement of the first head with surfaces of the first endplate that define the first cavity forms a first spheroidal joint; and
the second mating element comprises a second head that is disposed within a second cavity of the second endplate such that engagement of the second head with surfaces of the second endplate that define the second cavity forms a second spheroidal joint.

16. A spinal construct as recited in claim 14, wherein:
the first mating element comprises a first head that is disposed within a first cavity defined by a circumference of a first wall of the first endplate, the first wall comprising a first cutout that is in communication with the first cavity; and
the second mating element comprises a second head that is disposed within a second cavity defined by a circumference of a second wall of the second endplate, the second wall comprising a second cutout that is in communication with the second cavity.

17. A spinal construct as recited in claim 14, wherein:
the first mating element comprises a first ball that is disposed within a first socket of the first endplate such that the first ball and the first socket define a first ball and socket joint; and
the second mating element comprises a second ball that is disposed within a second socket of the second endplate such that the second ball and the second socket define a second ball and socket joint.

18. A spinal construct as recited in claim 14, wherein:
the first mating element comprises a first shaft having a thread form that engages with an end face of the inner body in threaded fixation; and
the second mating element comprises a second shaft having a thread form that engages with an end face of the outer body in threaded fixation.

19. A spinal construct as recited in claim 14, wherein:
the indentations extend into an outer surface of the inner body without extending through an opposite inner surface of the inner body; and
the indentations extend about only a portion of a circumference of the inner body.

20. A spinal construct comprising:
an expandable member including an outer body and an inner body movably positioned within an axial cavity of the outer body, the inner body comprising spaced apart indentations that each extend perpendicular to a longitudinal axis defined by the axial cavity, the indentations extending into an outer surface of the inner body without extending through an opposite inner surface of the inner body, the indentations extending about only a portion of a circumference of the inner body, the indentations being configured for engagement with a surgical instrument to facilitate axial translation of the inner body relative to the outer body;
a first mating element coupled to the inner body;
a second mating element coupled to the outer body;
a first endplate comprising a socket, a head of the first mating element being positioned within the socket such that the head and the socket define a ball and socket joint;
a second endplates comprising a socket, a head of the second mating element being positioned within the socket of the second endplate such that the head of the second mating element and the socket of the second endplate define a ball and socket joint; and
a spinal rod attachable with vertebral surfaces and a support connected with the expandable member and the spinal rod.

* * * * *